(12) United States Patent
Aranyi et al.

(10) Patent No.: US 7,931,660 B2
(45) Date of Patent: Apr. 26, 2011

(54) POWERED TACKER INSTRUMENT

(75) Inventors: Ernest Aranyi, Easton, CT (US); Gregg C. Krehel, Newtown, CT (US); Thomas Wenchell, Durham, CT (US); Earl M. Zergiebel, Guilford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 825 days.

(21) Appl. No.: 11/801,507

(22) Filed: May 10, 2007

(65) Prior Publication Data

US 2008/0281353 A1 Nov. 13, 2008

(51) Int. Cl.
*A61B 17/10* (2006.01)
*B25B 17/00* (2006.01)
*B25B 21/00* (2006.01)

(52) U.S. Cl. .................... 606/143; 81/57.37; 81/57.11

(58) Field of Classification Search .................. 606/142, 606/143, 139, 213, 104; 81/57.37, 431, 433, 81/435, 57.11, 54, 434; 173/216, 217; 227/175.1, 227/176.1, 179.1, 181.1, 175.2–175.4
See application file for complete search history.

(56) References Cited

U.S. PATENT DOCUMENTS

| | | | |
|---|---|---|---|
| 37,165 A | 12/1862 | Gary | |
| 2,256,012 A * | 9/1941 | Blair | 81/431 |
| 2,506,835 A * | 5/1950 | Johnson | 81/431 |
| 3,079,606 A | 3/1963 | Bobrov et al. | |
| 3,157,212 A * | 11/1964 | Raiteri | 81/431 |
| 3,209,754 A | 10/1965 | Brown | |
| 3,273,562 A | 9/1966 | Brown | |
| 3,299,499 A * | 1/1967 | Ruminsky | 29/413 |
| 3,421,557 A * | 1/1969 | Brauchla | 81/431 |
| 3,490,675 A | 1/1970 | Green et al. | |
| 3,499,591 A | 3/1970 | Green | |
| 3,528,466 A * | 9/1970 | Tracy | 81/431 |
| 3,528,693 A | 9/1970 | Pearson et al. | |
| 3,744,495 A | 7/1973 | Johnson | |
| 3,862,631 A | 1/1975 | Austin | |
| 3,949,924 A | 4/1976 | Green | |
| 4,060,089 A | 11/1977 | Noiles | |
| 4,204,623 A | 5/1980 | Green | |
| 4,217,902 A | 8/1980 | March | |

(Continued)

FOREIGN PATENT DOCUMENTS

EP 0 537 570 B1 4/1993

(Continued)

OTHER PUBLICATIONS

European Search Report dated Apr. 17, 2007 for Corresponding Patent Application EP06026840.

(Continued)

*Primary Examiner* — Julian W Woo
*Assistant Examiner* — Christopher L Templeton

(57) ABSTRACT

There is provided a powered tacker device for use in installing multiple surgical fasteners through a prosthetic mesh into tissue. The powered tacker device generally includes a handle assembly and a tacker assembly extending distally from the handle assembly. The handle assembly includes a motor and self-contained power assembly to rotate the surgical fasteners into tissue. The handle assembly is provided with a drive assembly which allows for rotation, as well as distal longitudinal movement, of a surgical fastener relative to the powered tacker device. The tacker assembly includes an inner tube for containing the plurality of surgical fasteners and a driver which is movable out of alignment with the inner tube so as to install a single fastener at a time into tissue.

13 Claims, 22 Drawing Sheets

U.S. PATENT DOCUMENTS

| | | | |
|---|---|---|---|
| 4,244,246 A * | 1/1981 | Gillett | 81/125 |
| 4,263,903 A | 4/1981 | Griggs | |
| 4,275,813 A | 6/1981 | Noiles | |
| 4,331,277 A | 5/1982 | Green | |
| 4,428,376 A | 1/1984 | Mericle | |
| 4,429,695 A | 2/1984 | Green | |
| 4,444,181 A | 4/1984 | Wevers et al. | |
| 4,454,875 A | 6/1984 | Pratt et al. | |
| 4,456,006 A | 6/1984 | Webers et al. | |
| 4,485,816 A | 12/1984 | Krumme | |
| 4,485,817 A | 12/1984 | Swiggett | |
| 4,488,523 A | 12/1984 | Shichman | |
| 4,508,253 A | 4/1985 | Green | |
| 4,508,523 A | 4/1985 | Leu | |
| 4,522,206 A | 6/1985 | Whipple et al. | |
| 4,534,350 A | 8/1985 | Goldman et al. | |
| 4,535,772 A | 8/1985 | Sheehan | |
| 4,566,620 A | 1/1986 | Green et al. | |
| 4,570,623 A | 2/1986 | Ellison et al. | |
| 4,606,343 A | 8/1986 | Conta et al. | |
| 4,606,344 A | 8/1986 | Di Giovanni | |
| 4,610,383 A | 9/1986 | Rothfuss et al. | |
| 4,612,923 A | 9/1986 | Kronenthal | |
| 4,612,933 A | 9/1986 | Brinkerhoff et al. | |
| D286,442 S | 10/1986 | Korthoff et al. | |
| 4,627,437 A | 12/1986 | Bedi et al. | |
| 4,635,637 A | 1/1987 | Schreiber | |
| 4,662,371 A | 5/1987 | Whipple et al. | |
| 4,671,280 A | 6/1987 | Dorband et al. | |
| 4,705,038 A | 11/1987 | Sjostrom et al. | |
| 4,712,550 A | 12/1987 | Sinnett | |
| 4,719,917 A | 1/1988 | Barrows et al. | |
| 4,724,839 A | 2/1988 | Bedi | |
| 4,805,617 A | 2/1989 | Bedi et al. | |
| 4,807,628 A | 2/1989 | Peters et al. | |
| 4,852,558 A | 8/1989 | Outerbridge | |
| 4,913,144 A | 4/1990 | DelMedico | |
| 4,960,420 A | 10/1990 | Goble et al. | |
| 4,962,877 A | 10/1990 | Hervas | |
| 4,990,153 A | 2/1991 | Richards | |
| 4,994,073 A | 2/1991 | Green | |
| 4,995,877 A | 2/1991 | Ams et al. | |
| 5,040,715 A | 8/1991 | Green et al. | |
| 5,065,929 A | 11/1991 | Schulze et al. | |
| 5,089,009 A | 2/1992 | Green | |
| 5,108,422 A | 4/1992 | Green et al. | |
| 5,114,399 A | 5/1992 | Kovalcheck | |
| 5,129,570 A | 7/1992 | Schulze et al. | |
| 5,143,453 A | 9/1992 | Weynant nee Girnes | |
| 5,203,864 A | 4/1993 | Phillips | |
| 5,207,697 A | 5/1993 | Carusillo et al. | |
| 5,209,756 A | 5/1993 | Seedhom et al. | |
| 5,246,443 A | 9/1993 | Mai | |
| 5,258,008 A | 11/1993 | Wilk | |
| 5,271,543 A | 12/1993 | Grant et al. | |
| RE34,519 E | 1/1994 | Fox et al. | |
| 5,282,829 A | 2/1994 | Hermes | |
| 5,300,081 A | 4/1994 | Young et al. | |
| 5,307,976 A | 5/1994 | Olson et al. | |
| 5,312,023 A | 5/1994 | Green et al. | |
| 5,312,024 A | 5/1994 | Grant et al. | |
| 5,313,935 A | 5/1994 | Kortenbach et al. | |
| 5,318,221 A | 6/1994 | Green et al. | |
| 5,326,013 A | 7/1994 | Green et al. | |
| 5,330,486 A | 7/1994 | Wilk | |
| 5,332,142 A | 7/1994 | Robinson et al. | |
| 5,342,376 A | 8/1994 | Ruff | |
| 5,350,355 A | 9/1994 | Sklar | |
| 5,352,229 A | 10/1994 | Goble et al. | |
| 5,354,292 A * | 10/1994 | Braeuer et al. | 606/1 |
| 5,356,064 A | 10/1994 | Green et al. | |
| 5,359,993 A | 11/1994 | Slater et al. | |
| 5,364,001 A | 11/1994 | Bryan | |
| 5,381,943 A | 1/1995 | Allen et al. | |
| 5,383,874 A | 1/1995 | Jackson et al. | |
| 5,383,880 A | 1/1995 | Hooven | |
| 5,389,098 A | 2/1995 | Tsuruta et al. | |
| 5,395,030 A | 3/1995 | Kuramoto et al. | |
| 5,395,033 A | 3/1995 | Byrne et al. | |
| 5,403,312 A | 4/1995 | Yates et al. | |
| 5,405,344 A | 4/1995 | Williamson et al. | |
| 5,411,508 A | 5/1995 | Bessler et al. | |
| 5,413,267 A | 5/1995 | Solyntjes et al. | |
| 5,431,323 A | 7/1995 | Smith et al. | |
| 5,464,144 A | 11/1995 | Guy et al. | |
| 5,467,911 A | 11/1995 | Tsuruta et al. | |
| 5,478,344 A | 12/1995 | Stone et al. | |
| 5,482,100 A | 1/1996 | Kuhar | |
| 5,485,947 A | 1/1996 | Olson et al. | |
| 5,487,499 A | 1/1996 | Sorrentino et al. | |
| 5,497,933 A | 3/1996 | DeFonzo et al. | |
| 5,500,000 A | 3/1996 | Feagin et al. | |
| 5,503,320 A | 4/1996 | Webster et al. | |
| 5,507,743 A | 4/1996 | Edwards et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,531,744 A | 7/1996 | Nardella et al. | |
| 5,533,661 A | 7/1996 | Main et al. | |
| 5,535,934 A | 7/1996 | Boiarski et al. | |
| 5,535,937 A | 7/1996 | Boiarski et al. | |
| 5,558,671 A | 9/1996 | Yates | |
| 5,560,532 A | 10/1996 | DeFonzo et al. | |
| 5,562,239 A | 10/1996 | Boiarski et al. | |
| 5,571,285 A | 11/1996 | Chow et al. | |
| 5,575,799 A | 11/1996 | Bolanos et al. | |
| 5,582,611 A | 12/1996 | Tsuruta et al. | |
| 5,582,616 A * | 12/1996 | Bolduc et al. | 606/143 |
| 5,584,835 A | 12/1996 | Greenfield | |
| 5,601,224 A | 2/1997 | Bishop et al. | |
| 5,601,558 A | 2/1997 | Torrie et al. | |
| 5,607,095 A | 3/1997 | Smith et al. | |
| 5,609,285 A | 3/1997 | Grant et al. | |
| 5,609,560 A | 3/1997 | Ichikawa et al. | |
| 5,624,452 A | 4/1997 | Yates | |
| 5,632,433 A | 5/1997 | Grant et al. | |
| 5,634,926 A | 6/1997 | Jobe | |
| 5,642,848 A | 7/1997 | Ludwig et al. | |
| 5,653,374 A | 8/1997 | Young et al. | |
| 5,658,300 A | 8/1997 | Bito et al. | |
| 5,658,312 A | 8/1997 | Green et al. | |
| 5,662,662 A | 9/1997 | Bishop et al. | |
| 5,665,085 A | 9/1997 | Nardella | |
| 5,667,513 A | 9/1997 | Torrie et al. | |
| 5,667,517 A | 9/1997 | Hooven | |
| 5,667,527 A | 9/1997 | Cook | |
| 5,669,544 A | 9/1997 | Schulze et al. | |
| 5,673,841 A | 10/1997 | Schulze et al. | |
| 5,676,674 A | 10/1997 | Bolanos et al. | |
| 5,680,981 A | 10/1997 | Mililli et al. | |
| 5,680,982 A | 10/1997 | Schulze et al. | |
| 5,692,668 A | 12/1997 | Schulze et al. | |
| 5,695,524 A | 12/1997 | Kelley et al. | |
| 5,702,447 A | 12/1997 | Walch et al. | |
| 5,704,534 A | 1/1998 | Huitema et al. | |
| 5,713,505 A | 2/1998 | Huitema | |
| 5,713,896 A | 2/1998 | Nardella | |
| 5,715,987 A | 2/1998 | Kelley et al. | |
| 5,716,366 A | 2/1998 | Yates | |
| 5,720,753 A | 2/1998 | Sander et al. | |
| 5,725,529 A | 3/1998 | Nicholson et al. | |
| 5,728,110 A | 3/1998 | Vidal et al. | |
| 5,728,116 A | 3/1998 | Rosenman | |
| 5,730,757 A | 3/1998 | Nenetti et al. | |
| 5,735,848 A | 4/1998 | Yates et al. | |
| 5,735,854 A * | 4/1998 | Caron et al. | 606/916 |
| 5,738,474 A | 4/1998 | Blewett | |
| 5,755,726 A | 5/1998 | Pratt | |
| 5,759,171 A | 6/1998 | Coelho et al. | |
| 5,779,130 A | 7/1998 | Alesi et al. | |
| 5,785,713 A | 7/1998 | Jobe | |
| 5,788,698 A | 8/1998 | Savornin | |
| 5,810,811 A | 9/1998 | Yates et al. | |
| 5,823,066 A | 10/1998 | Huitema et al. | |
| 5,829,662 A | 11/1998 | Allen et al. | |
| 5,830,121 A | 11/1998 | Enomoto et al. | |

| | | | | | | |
|---|---|---|---|---|---|---|
| 5,830,221 | A | 11/1998 | Stein et al. | 6,315,184 B1 | 11/2001 | Whitman |
| 5,849,023 | A | 12/1998 | Mericle | 6,329,778 B1 | 12/2001 | Culp et al. |
| 5,849,028 | A | 12/1998 | Chen | 6,330,965 B1 | 12/2001 | Milliman et al. |
| 5,855,311 | A | 1/1999 | Hamblin et al. | 6,346,104 B2 | 2/2002 | Daly et al. |
| 5,861,005 | A | 1/1999 | Kontos | 6,355,066 B1 | 3/2002 | Kim |
| 5,865,361 | A | 2/1999 | Milliman et al. | 6,364,884 B1 | 4/2002 | Bowman et al. |
| 5,876,401 | A | 3/1999 | Schulze et al. | 6,387,092 B1 | 5/2002 | Burnside et al. |
| 5,891,156 | A | 4/1999 | Gessner et al. | 6,388,240 B2 | 5/2002 | Schulz et al. |
| 5,893,813 | A | 4/1999 | Yamamoto | 6,402,759 B1 * | 6/2002 | Strong et al. .................. 606/104 |
| 5,895,396 | A | 4/1999 | Day et al. | 6,402,766 B2 | 6/2002 | Bowman et al. |
| 5,906,607 | A | 5/1999 | Taylor et al. | H2037 H | 7/2002 | Yates et al. |
| 5,911,721 | A | 6/1999 | Nicholson et al. | 6,412,279 B1 | 7/2002 | Coleman et al. |
| 5,918,791 | A | 7/1999 | Sorrentino et al. | 6,425,903 B1 | 7/2002 | Voegele |
| 5,928,222 | A | 7/1999 | Kleinerman | 6,436,097 B1 | 8/2002 | Nardella |
| 5,944,717 | A | 8/1999 | Lee et al. | 6,436,107 B1 | 8/2002 | Wang et al. |
| 5,944,736 | A | 8/1999 | Taylor et al. | 6,436,110 B1 | 8/2002 | Bowman et al. |
| 5,954,259 | A | 9/1999 | Viola et al. | 6,443,973 B1 | 9/2002 | Whitman |
| 5,961,521 | A | 10/1999 | Roger | 6,447,517 B1 | 9/2002 | Bowman |
| 5,964,394 | A | 10/1999 | Robertson | 6,461,372 B1 | 10/2002 | Jensen et al. |
| 5,968,044 | A | 10/1999 | Nicholson et al. | 6,478,210 B2 | 11/2002 | Adams et al. |
| 5,976,171 | A | 11/1999 | Taylor | 6,497,707 B1 | 12/2002 | Bowman et al. |
| 5,980,518 | A | 11/1999 | Carr et al. | 6,505,768 B2 | 1/2003 | Whitman |
| 5,980,548 | A | 11/1999 | Evans et al. | 6,515,273 B2 | 2/2003 | Al-Ali |
| 5,991,355 | A | 11/1999 | Dahlke | 6,524,316 B1 | 2/2003 | Nicholson et al. |
| 5,991,650 | A | 11/1999 | Swanson et al. | 6,533,157 B1 | 3/2003 | Whitman |
| 5,992,724 | A | 11/1999 | Snyder | 6,540,751 B2 | 4/2003 | Enayati |
| 5,997,552 | A | 12/1999 | Person et al. | 6,544,273 B1 | 4/2003 | Harari et al. |
| 6,004,335 | A | 12/1999 | Vaitekunas et al. | 6,554,852 B1 | 4/2003 | Oberlander |
| 6,007,550 | A | 12/1999 | Wang et al. | 6,562,071 B2 | 5/2003 | Jarvinen |
| 6,010,054 | A | 1/2000 | Johnson et al. | 6,578,579 B2 | 6/2003 | Burnside et al. |
| 6,013,077 | A | 1/2000 | Harwin | 6,578,750 B2 * | 6/2003 | Kubo et al. .................. 227/142 |
| 6,015,417 | A | 1/2000 | Reynolds, Jr. | 6,601,748 B1 | 8/2003 | Fung et al. |
| 6,017,354 | A | 1/2000 | Culp et al. | 6,601,749 B2 | 8/2003 | Sullivan et al. |
| 6,030,410 | A | 2/2000 | Zurbrugg | 6,602,252 B2 | 8/2003 | Mollenauer |
| 6,032,849 | A | 3/2000 | Mastri et al. | 6,611,793 B1 | 8/2003 | Burnsude et al. |
| 6,039,731 | A | 3/2000 | Taylor et al. | 6,616,821 B2 | 9/2003 | Broadley et al. |
| 6,051,007 | A | 4/2000 | Hogendijk | 6,629,986 B1 | 10/2003 | Ross et al. |
| 6,063,078 | A | 5/2000 | Wittkampf | 6,651,669 B1 | 11/2003 | Burnside |
| 6,063,095 | A | 5/2000 | Wang et al. | 6,656,177 B2 | 12/2003 | Truckai et al. |
| 6,077,246 | A | 6/2000 | Kullas et al. | 6,669,073 B2 | 12/2003 | Milliman et al. |
| 6,079,606 | A | 6/2000 | Milliman et al. | 6,669,705 B2 | 12/2003 | Westhaver et al. |
| 6,080,150 | A | 6/2000 | Gough | 6,696,008 B2 | 2/2004 | Brandinger |
| 6,083,242 | A | 7/2000 | Cook | 6,698,643 B2 | 3/2004 | Whitman |
| 6,090,123 | A | 7/2000 | Culp et al. | 6,699,177 B1 | 3/2004 | Wang et al. |
| 6,092,422 | A | 7/2000 | Binnig et al. | 6,716,233 B1 | 4/2004 | Whitman |
| 6,109,500 | A | 8/2000 | Alli et al. | 6,736,085 B1 | 5/2004 | Esnouf |
| 6,113,592 | A | 9/2000 | Taylor | 6,792,390 B1 | 9/2004 | Burnside et al. |
| 6,123,702 | A | 9/2000 | Swanson et al. | 6,817,508 B1 | 11/2004 | Racenet et al. |
| H1904 | H | 10/2000 | Yates et al. | 6,830,174 B2 | 12/2004 | Hillstead et al. |
| 6,126,058 | A | 10/2000 | Adams et al. | 6,843,403 B2 | 1/2005 | Whitman |
| 6,126,651 | A | 10/2000 | Mayer | 6,846,307 B2 | 1/2005 | Whitman et al. |
| 6,127,811 | A | 10/2000 | Shenoy et al. | 6,846,308 B2 | 1/2005 | Whitman et al. |
| 6,132,425 | A | 10/2000 | Gough | 6,846,309 B2 | 1/2005 | Whitman et al. |
| 6,165,169 | A | 12/2000 | Panescu et al. | 6,849,071 B2 | 2/2005 | Whitman et al. |
| 6,166,538 | A | 12/2000 | D'Alfonso | 6,861,639 B2 | 3/2005 | Al-Ali |
| 6,179,840 | B1 | 1/2001 | Bowman | 6,872,214 B2 | 3/2005 | Sonnenschein et al. |
| 6,187,009 | B1 | 2/2001 | Herzog et al. | 6,899,538 B2 | 5/2005 | Matoba |
| 6,187,019 | B1 | 2/2001 | Stefanchik et al. | 6,900,004 B2 | 5/2005 | Satake |
| 6,190,401 | B1 | 2/2001 | Green et al. | 6,905,057 B2 | 6/2005 | Swayze et al. |
| 6,193,501 | B1 | 2/2001 | Masel et al. | 6,926,636 B2 | 8/2005 | Luper |
| 6,202,914 | B1 | 3/2001 | Geiste et al. | 6,953,139 B2 | 10/2005 | Millimam et al. |
| 6,217,573 | B1 | 4/2001 | Webster | 6,959,852 B2 | 11/2005 | Shelton et al. |
| 6,228,534 | B1 | 5/2001 | Takeuchi et al. | 6,979,328 B2 | 12/2005 | Baerveldt et al. |
| 6,231,565 | B1 | 5/2001 | Tovey et al. | 6,981,628 B2 | 1/2006 | Wales |
| 6,236,874 | B1 | 5/2001 | Declin et al. | 6,981,941 B2 | 1/2006 | Whitman et al. |
| 6,237,604 | B1 | 5/2001 | Burnside et al. | 6,988,649 B2 | 1/2006 | Shelton et al. |
| 6,241,139 | B1 | 6/2001 | Milliman et al. | 7,000,819 B2 | 2/2006 | Swayze et al. |
| 6,245,065 | B1 | 6/2001 | Panescu et al. | 7,032,798 B2 | 4/2006 | Whitman et al. |
| 6,248,117 | B1 | 6/2001 | Blatter | 7,044,353 B2 | 5/2006 | Mastri et al. |
| 6,250,532 | B1 | 6/2001 | Green et al. | 7,048,687 B1 | 5/2006 | Reuss et al. |
| 6,258,111 | B1 | 7/2001 | Ross et al. | 7,059,508 B2 | 6/2006 | Shelton et al. |
| 6,264,086 | B1 | 7/2001 | McGuckin, Jr. | 7,077,856 B2 | 7/2006 | Whitman |
| 6,264,087 | B1 | 7/2001 | Whitman | 7,083,075 B2 | 8/2006 | Swayze et al. |
| 6,264,653 | B1 | 7/2001 | Falwell | 7,097,089 B2 | 8/2006 | Marczyk |
| 6,281,471 | B1 | 8/2001 | Smart | 7,111,769 B2 | 9/2006 | Wales et al. |
| 6,288,534 | B1 | 9/2001 | Starkweather et al. | 7,118,564 B2 | 10/2006 | Ritchie et al. |
| 6,290,701 | B1 | 9/2001 | Enayati | 7,122,029 B2 | 10/2006 | Koop et al. |
| 6,293,943 | B1 | 9/2001 | Panescu et al. | 7,128,253 B2 | 10/2006 | Mastri et al. |
| 6,295,330 | B1 | 9/2001 | Skog et al. | 7,128,254 B2 | 10/2006 | Shelton et al. |

| | | |
|---|---|---|
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Jorzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smirh et al. |
| 7,422,136 B1 | 9/2008 | Marczyk |
| 7,461,574 B2 * | 12/2008 | Lewis et al. ............... 81/57.37 |
| 7,464,846 B2 | 12/2008 | Shelton, IV et al. |
| 7,464,847 B2 * | 12/2008 | Viola et al. ............... 227/175.2 |
| 2002/0025891 A1 | 2/2002 | Colosky et al. |
| 2002/0103489 A1 | 8/2002 | Ku |
| 2002/0111641 A1 | 8/2002 | Peterson et al. |
| 2002/0165541 A1 | 11/2002 | Whitman |
| 2003/0073981 A1 | 4/2003 | Whitman et al. |
| 2003/0114851 A1 | 6/2003 | Truckai et al. |
| 2003/0120306 A1 | 6/2003 | Burbank et al. |
| 2003/0139746 A1 | 7/2003 | Groiso |
| 2004/0094597 A1 | 5/2004 | Whitman et al. |
| 2004/0232199 A1 | 11/2004 | Shelton, IV et al. |
| 2004/0232201 A1 | 11/2004 | Wenchell et al. |
| 2005/0006429 A1 | 1/2005 | Wales et al. |
| 2005/0006430 A1 | 1/2005 | Wales |
| 2005/0006431 A1 | 1/2005 | Shelton, IV et al. |
| 2005/0006434 A1 | 1/2005 | Wales et al. |
| 2005/0010235 A1 | 1/2005 | VanDusseldorp |
| 2005/0023324 A1 | 2/2005 | Doll et al. |
| 2005/0067458 A1 | 3/2005 | Swayze et al. |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0131390 A1 | 6/2005 | Heinrich et al. |
| 2005/0139636 A1 | 6/2005 | Schwemberger et al. |
| 2005/0145674 A1 | 7/2005 | Sonnenschein et al. |
| 2005/0177176 A1 | 8/2005 | Gerbi et al. |
| 2005/0178813 A1 | 8/2005 | Swayze et al. |
| 2005/0187576 A1 | 8/2005 | Whitman et al. |
| 2005/0187613 A1 * | 8/2005 | Bolduc et al. ............... 623/1.23 |
| 2005/0192609 A1 | 9/2005 | Whitman et al. |
| 2005/0228341 A1 | 10/2005 | Edgerley |
| 2005/0247753 A1 | 11/2005 | Kelly et al. |
| 2005/0251201 A1 * | 11/2005 | Roue et al. ............... 606/213 |
| 2005/0267478 A1 * | 12/2005 | Corradi et al. ............... 606/73 |
| 2006/0000867 A1 | 1/2006 | Shelton, IV et al. |
| 2006/0022014 A1 | 2/2006 | Shelton, IV |
| 2006/0022015 A1 | 2/2006 | Shelton, IV |
| 2006/0097025 A1 | 5/2006 | Milliman et al. |
| 2006/0151567 A1 | 7/2006 | Roy |
| 2006/0175375 A1 | 8/2006 | Shelton, IV |
| 2006/0241622 A1 | 10/2006 | Zergiebel |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0029364 A1 | 2/2007 | Kruszynski et al. |
| 2007/0039995 A1 | 2/2007 | Schwemberger et al. |
| 2007/0039996 A1 | 2/2007 | Mather et al. |
| 2007/0039997 A1 | 2/2007 | Mather et al. |
| 2007/0084896 A1 | 4/2007 | Doll et al. |
| 2007/0084897 A1 | 4/2007 | Shelton, IV et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102475 A1 | 5/2007 | Ortiz et al. |
| 2007/0125826 A1 | 6/2007 | Shelton, IV |
| 2007/0152014 A1 | 7/2007 | Gillum et al. |
| 2007/0158385 A1 | 7/2007 | Hueil et al. |
| 2007/0175947 A1 | 8/2007 | Ortiz et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV |
| 2007/0175953 A1 | 8/2007 | Shelton, IV |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV |
| 2007/0175958 A1 | 8/2007 | Shelton, IV |
| 2007/0175959 A1 | 8/2007 | Shelton, IV |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0187453 A1 | 8/2007 | Smith et al. |
| 2007/0219563 A1 | 9/2007 | Voegele |
| 2007/0265640 A1 | 11/2007 | Kortenbach et al. |
| 2007/0278277 A1 | 12/2007 | Wixey et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0110957 A1 | 5/2008 | McBride et al. |
| 2008/0135600 A1 | 6/2008 | Hiranuma et al. |
| 2008/0164296 A1 | 7/2008 | Shelton et al. |
| 2008/0169329 A1 | 7/2008 | Shelton et al. |
| 2008/0185419 A1 | 8/2008 | Smith et al. |

FOREIGN PATENT DOCUMENTS

| | | |
|---|---|---|
| EP | 0 647 431 B1 | 4/1995 |
| EP | 0 738 501 A1 | 10/1996 |
| EP | 0770354 A1 | 10/1996 |
| EP | 1070487 A2 | 1/2001 |
| EP | 1 813 203 A | 8/2007 |
| EP | 1970915 | 9/2008 |
| EP | 2044890 | 4/2009 |
| WO | WO 97/29694 | 8/1997 |
| WO | WO 97/40760 A1 | 11/1997 |
| WO | WO 98/37825 | 9/1998 |
| WO | WO 99/52489 A1 | 10/1999 |
| WO | WO 02/34140 A2 | 5/2002 |
| WO | WO 03/030743 A2 | 10/2002 |
| WO | WO 03/026511 | 4/2003 |
| WO | WO 2004/032760 A2 | 4/2004 |
| WO | WO 2007/030753 A2 | 3/2007 |
| WO | WO 2007/118179 A2 | 10/2007 |

OTHER PUBLICATIONS

International Search Report for corresponding PCT Application—PCT/US06/21524—Date of Mailing May 28, 2008 (4 Pages).

Detemple, P., "Microtechnology in Modern Health Care", *Med Device Technol.* 9(9):18-25 (1998).

European Search Report for corresponding EP 08252703.7 dated Oct. 31, 2008 (3 pages).

European Search Report dated Feb. 27, 2009 for Corresponding Patent Application 08253184.9.

European Search Report for corresponding EP 08252703.7 dated Oct. 31, 2008 (7 pages).

European Search Report for corresponding EP 08251357 date of mailing is Sep. 29, 2009 (3 pages).

European Search Report for corresponding EP 08253489 date of mailing is Sep. 29, 2009 (3 pages).

European Search Report for EP 08251665.9-2310 date of completion is Apr. 19, 2010 (3 pages).

* cited by examiner

POWERED TACKER INSTRUMENT

BACKGROUND

1. Technical Field

The present disclosure relates to a surgical instrument for installing fasteners into tissue. More particularly, the present disclosure relates to a powered tacker instrument for use in applying surgical fasteners through a prosthetic mesh and into tissue during hernia repair surgery.

2. Background of Related Art

Various surgical procedures require instruments capable of applying fasteners to tissue to form tissue connections or to secure objects to tissue. For example, during hernia repair procedures it is often desirable to fasten a mesh to body tissue. In certain hernias, such as direct or indirect inguinal hernias, a part of the intestine protrudes through a defect in the abdominal wall to form a hernial sac. The defect may be repaired using an open surgery procedure in which a relatively large incision is made and the hernia is closed off outside the abdominal wall by suturing. The mesh is attached with sutures over the opening to provide reinforcement.

Less invasive surgical procedures are currently available to repair a hernia. For example, in laparoscopic procedures, the hernia repair surgery is performed through a small incision in the abdomen while in endoscopic procedures, the hernia repair surgery is performed through narrow endoscopic tubes or cannulas inserted through small incisions in the body. Laparoscopic and endoscopic procedures generally require the use of long and narrow surgical instruments capable of reaching deep within the body and configured to seal with the incision or tube they are inserted through. Additionally, the instruments must be capable of being actuated remotely, that is, from outside the body.

Currently, endoscopic techniques for hernia repair utilize fasteners, such as, surgical staples or clips, to secure the mesh to the tissue to provide reinforcement in the repair and structure for encouraging tissue regrowth. The staples or clips are compressed against the tissue and mesh to secure the two together.

One other type of fastener suited for use in affixing mesh to tissue, during procedures such as hernia repair, is a coil fastener having a helically coiled body portion terminating in a tissue penetrating tip or a hollow screw type fastener having an external thread. Unique instruments have been developed to rotate these fasteners into tissue. Examples of some of these types of surgical fasteners and surgical instruments are disclosed in U.S. Pat. Nos. 5,258,000 and 5,830,221, the contents of which are incorporated by reference herein.

Most surgical instruments for applying fasteners to tissue can be actuated without the distal end of the surgical instrument actually in contact with tissue. This may result in a fastener being inadvertently ejected prior to placement against tissue or only partially installed in tissue.

In hernia repair surgery it is necessary to place multiple fasteners through a prosthetic mesh and into tissue. Often it is necessary to actuate the surgical instrument several times to rotate a single fastener through the mesh and into tissue. This can cause fatigue in the operator's hand. Additionally, it may be necessary to use a large amount of force on the actuator to install the fastener through various stiffness meshes resulting in further fatigue to the user's hand.

Thus, there is a need for a surgical instrument which can not be actuated to apply a fastener until the surgical instrument is securely positioned against the target tissue.

Furthermore, there is also need for a surgical instrument which has a power source to easily and comfortably install multiple fasteners and provide sufficient torque to drive the fasteners through a prosthetic mesh and into tissue.

SUMMARY

There is disclosed a powered tacker device having a handle assembly and a tacker assembly extending distally from the handle assembly. The handle assembly includes a power source and a drive assembly mounted within the handle assembly. The drive assembly includes a keyed journal rotatably mounted within the handle assembly and rotatable in response to actuation of the power source. The drive assembly further includes a drive bar longitudinally movable relative to the keyed journal and rotatable in response to rotation of the keyed journal. The tacker assembly includes an inner tube terminating in a driver engageable with a fastener contained within the driver. The inner tube is connected to the rotator and rotatable in response to rotation of the keyed journal. The powered tacker device additionally includes an actuator associated with the handle assembly and operable to engage the power source with the drive assembly.

The keyed journal includes a threaded bore and the drive rod includes a threaded outer surface engageable with the threaded bore. Rotation of the keyed journal within the handle assembly moves the drive rod in a longitudinal direction within the handle assembly. The drive bar is connected to the rotator to move the rotator longitudinally within the handle assembly in response to rotation of the keyed journal. Keyed journal further includes distally extending keys. The rotator includes slots engageable with the keys such that the rotator is rotated in response to rotation of the keyed journal. In one embodiment, the rotator is longitudinally movable along the keys.

In one embodiment, the handle assembly includes a first limit switch and a second limit switch. The first and second limit switches are operable to deactivate the power source from the drive assembly. The drive rod includes a contact assembly which is engageable with the first limit switch when the drive bar is in a proximal most position and engageable with the second limit switch when the drive bar is in a distal most position. The handle assembly includes at least one indicator providing a visual indication when the contact assembly has engaged one of the limit switches.

In one embodiment, the power source includes a motor engageable with the keyed journal so as to rotate the keyed journal and a battery to power the motor. The drive assembly includes a drive gear engageable with the keyed journal to rotate the keyed journal. The drive gear is engageable with a spur gear on the motor to rotate the keyed journal.

In one embodiment, the drive assembly includes a mesh gear engageable with the keyed journal and the drive gear. The drive assembly includes a spring to bias the mesh gear into engagement with the keyed journal. The spring allows the mesh gear to disengage from the drive gear to prevent over rotation of the keyed journal.

The handle assembly includes a safety mechanism preventing actuation of the power source prior to the proper positioning of the powered tacker device relative to tissue. The safety mechanism includes an outer tube mounted for longitudinal movement relative to the handle assembly and a safety switch actuable in response to movement of the outer tube. The safety switch prevents actuation of the power source when the outer tube is in the distal most position.

There is also disclosed a powered tacker device having a handle assembly and a tacker assembly extending distally from the handle assembly. The handle assembly includes a power source in the drive assembly mounted for rotation within the handle assembly and rotatable in response to activation of the power source. The tacker assembly includes an inner tube containing a plurality of surgical fasteners and connected to the drive assembly. A driver is mounted on the distal end of the in the tube to rotate the surgical fasteners into tissue. The inner tube is rotatable a limited predetermined initial amount relative to the driver. The tacker assembly includes a spring positioned intermediate the inner two and driver to bias the inner tube relative to the driver.

In one embodiment, the inner tube includes a longitudinally extending transfer bar is configured to maintain the surgical fasteners in a predetermined orientation. The driver includes tabs engageable with the surgical fasteners to drive the surgical fasteners into tissue. The inner tube is rotatable relative to the driver to move the transfer bar into and out of alignment with the drive tabs. This allows only one fastener at a time to be positioned within the driver while the driver drives the faster into tissue. Once the transfer bars have been realigned with the drive tabs a subsequent fastener may be advanced from within the inner tube and into the driver.

DESCRIPTION OF THE DRAWINGS

An embodiment of the presently disclosed powered tacker device is described herein with reference to the drawings, wherein:

FIG. 7a is a perspective, partial exploded view of a portion of the powered tacker device including a spring retainer;

FIG. 8a is a perspective view of a driver;

DETAILED DESCRIPTION OF EMBODIMENTS

An embodiment of the presently disclosed powered tacker device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
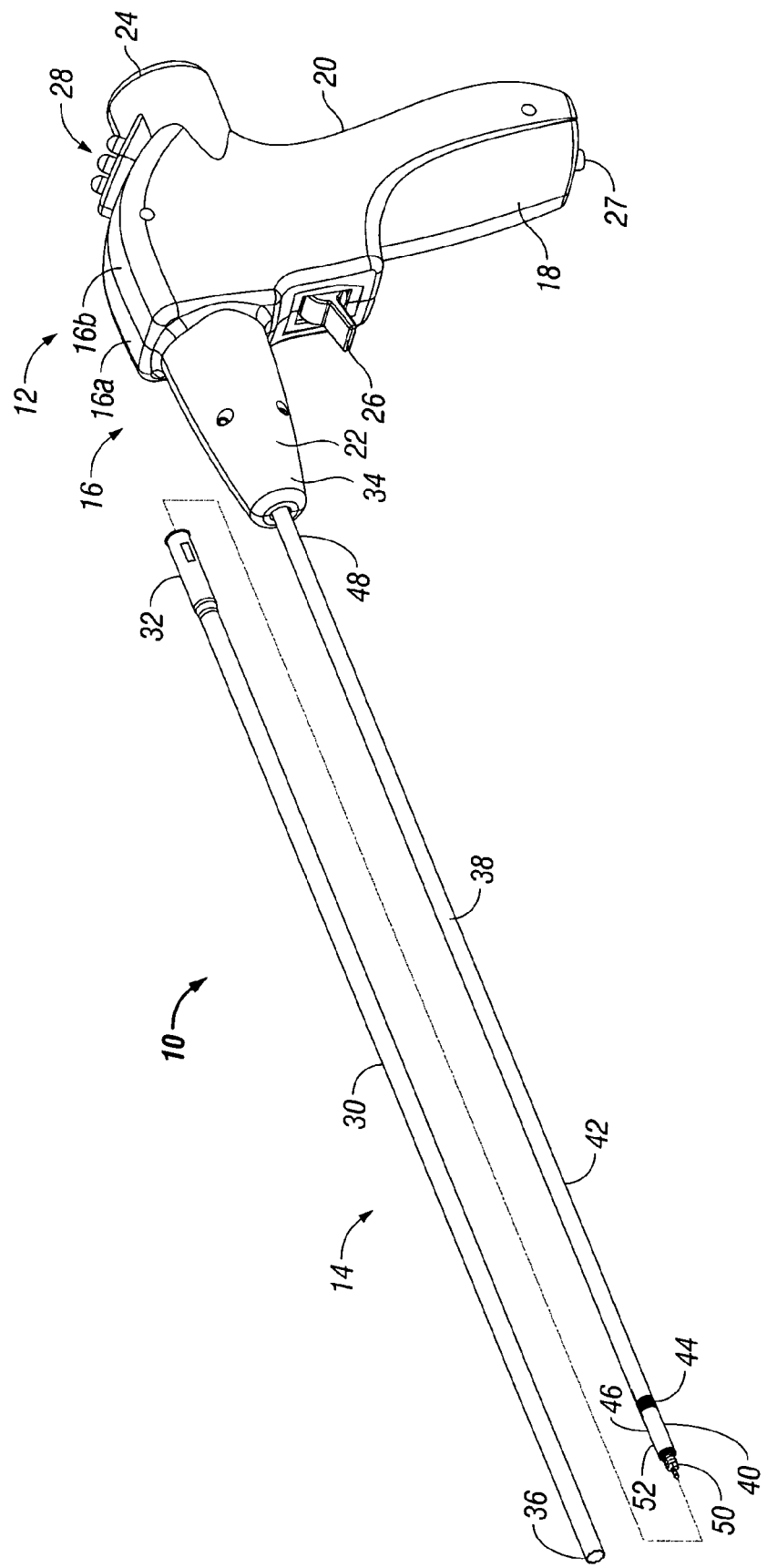
FIG. 1 is a perspective view of a powered tacker device with an outer tube separated.

Referring to FIG. 1, there is disclosed a powered tacking instrument, or powered tacker 10, for use in installing surgical fasteners in tissue. Powered tacker 10 generally includes a handle assembly 12 and an elongate distal tacker assembly 14 extending distally from handle assembly 12. Handle assembly 12 includes a handle housing 16 which is formed from two housing halves 16a and 16b. Handle housing 16 has a grip portion 18, a body portion 20 and a nose cone portion 22 extending distally from body portion 20. Handle assembly 12 has a motor 24, mounted in body portion 20, which powers powered tacker 10 to drive surgical fasteners into tissue. A trigger 26 is mounted in body portion 20 to actuate motor 24 in a manner described in more detail hereinbelow. Handle assembly 12 may also include an indicator or light assembly 28, which is provided to indicate the status of the various cycles and/or operational status of powered tacker 10. It is also envisioned that a switch 27 (e.g., a push-button switch in FIG. 1) may be used to turn powered tacker 10 on and off.

Distal tacker assembly 14 includes an outer tube 30 which is mounted for movement relative to handle assembly 12. Specifically, a proximal end 32 is movably mounted through an open distal end 34 of nose cone portion 22. Engagement of a distal end 36 of outer tube 30 with tissue moves outer tube 30 relative to handle assembly 12 to activate a lockout or safety mechanism as described hereinbelow. An inner tube 38 is positioned within outer tube 30 and also extends distally from handle assembly 12. A driver 40 is positioned on a distal end 42 of inner tube 38 such that driver 40 can be rotated by inner tube 38 in response to activation of powered tacker 10. A torsion spring 44 is connected to, and positioned between, a proximal end 46 of driver 40 and a distal end 48 of inner tube 38 to allow driver to have a limited amount of reversible rotation relative to inner tube 38. This limited amount of reversible rotation assists in managing the advancement of a fastener 50 from inner tube 38 into driver 40, out a distal end 52 of driver 40, and into tissue.

Figure 2:
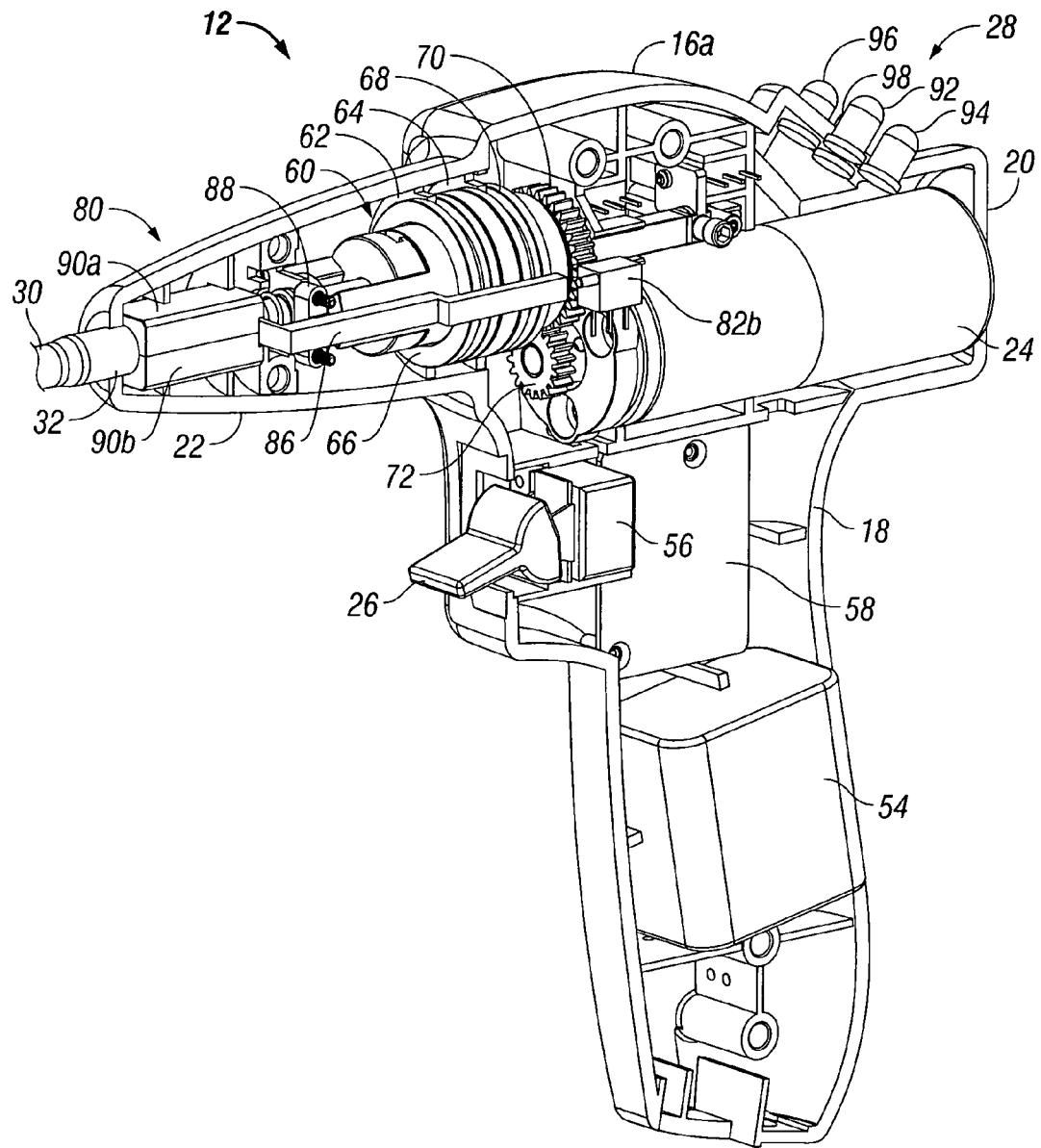
FIG. 2 is a perspective view of a handle assembly of the powered tacker device with half of a handle housing removed.
Figure 3:
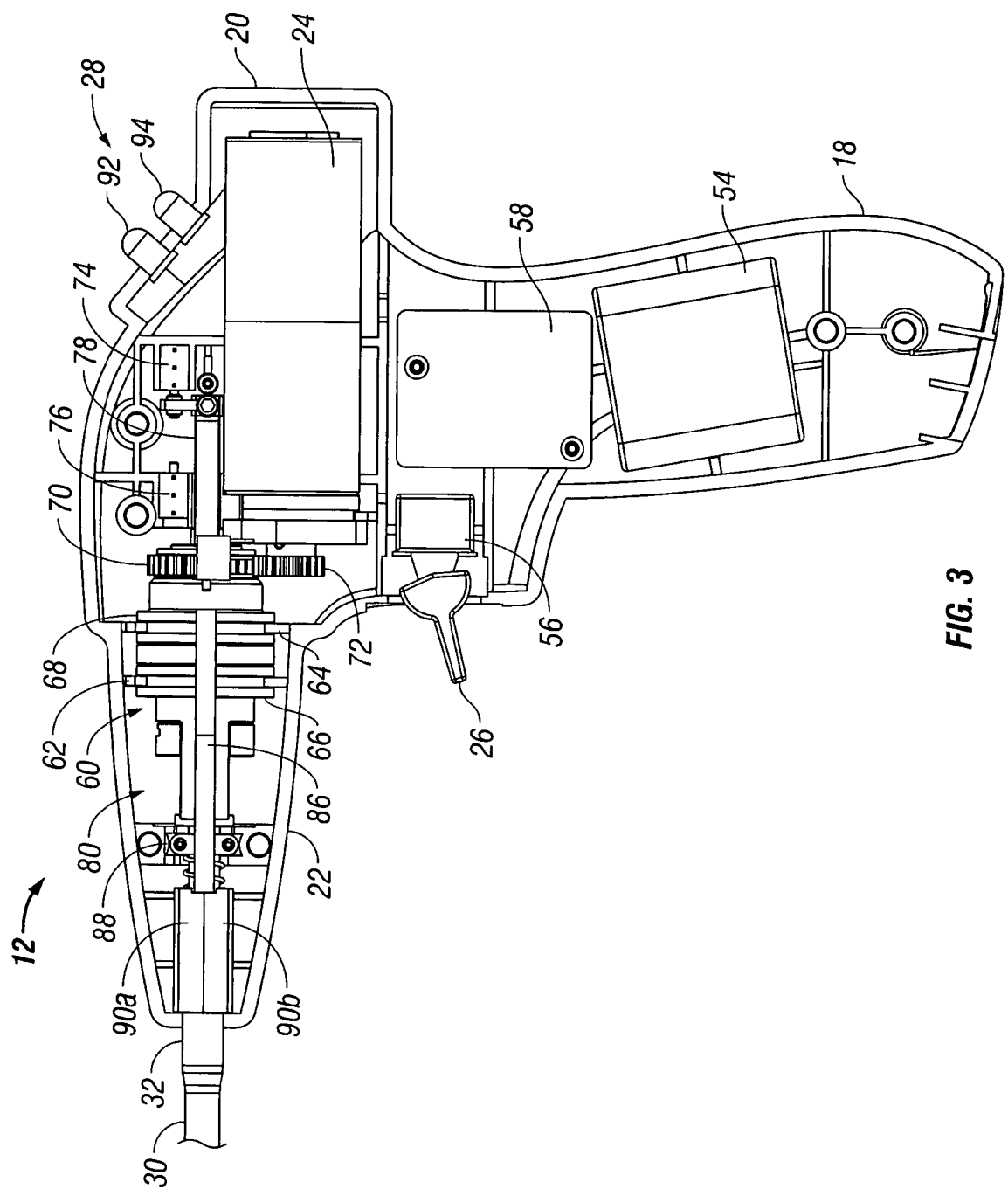
FIG. 3 is a side view of the handle assembly with half of the handle housing removed.

Referring now to FIGS. 2 and 3, as noted above, handle assembly 12 includes a motor 24 which is provided to rotate and advance inner tube 38 in response to actuation of trigger 26 in order to install a surgical fastener into tissue. Handle assembly 12 includes a battery 54 to powered motor 24. A trigger switch 56 is provided on grip portion 18 and is actuated by trigger 26 in order to operate motor 24. Trigger switch 56 may be a multiposition type switch allowing actuation of motor 24 in both a forward and reverse direction. Handle assembly 12 additionally includes a circuit board 58 which is provided to control the electronics of powered tacker 10. In addition to managing the flow of current from battery 54 through trigger switch 56 and to motor 24, circuit board 58 additionally acts as the "brain" of powered tacker 10. Circuit board 58 receives signals from various safety and motion limiting switches and displays the various operational status conditions of powered tacker 10 by means of indicator light assembly 28.

As noted hereinabove, inner tube 38 is rotatably mounted to handle assembly 12 so as to drive a surgical fastener into tissue. Handle assembly 12 contains a drive assembly 60 which is rotatably mounted within handle assembly 12. Drive assembly 60 rotates, as well as moves longitudinally, inner tube 38 in response to actuation of trigger 26. Drive assembly 60 is rotatably mounted on first and second housing flanges 62 and 64 formed in handle housing halves 16a and 16b. Specifically, drive assembly 60 includes a distal journal 66 which is rotatably mounted in first housing flange 62 and a proximal journal 68 which is rotatably mounted within second housing flange 64. In order to rotate drive assembly 60, drive assembly 60 includes a drive gear 70 which is engageable with a worm gear 72 provided on motor 24.

In order to ensure that inner tube 38 rotates and translates within predetermined parameters, handle assembly 12 includes a proximal limit switch 74 and a distal limit switch 76. Limit switches 74 and 76 are electronically connected to motor 24 through circuit board 58. It should be noted that, while not specifically shown, the various electronic components of powered tacker 10 are wired or connected in known manner to achieve the various switching and display functions. Proximal limit switch 74 corresponds to the initial or unactuated condition of powered tacker 10 while distal limit switch 76 corresponds to the fully actuated condition of powered tacker 10. A contact arm 78 is associated with drive assembly 60 to engage proximal and distal limit switches 74 and 76.

Figure 4:
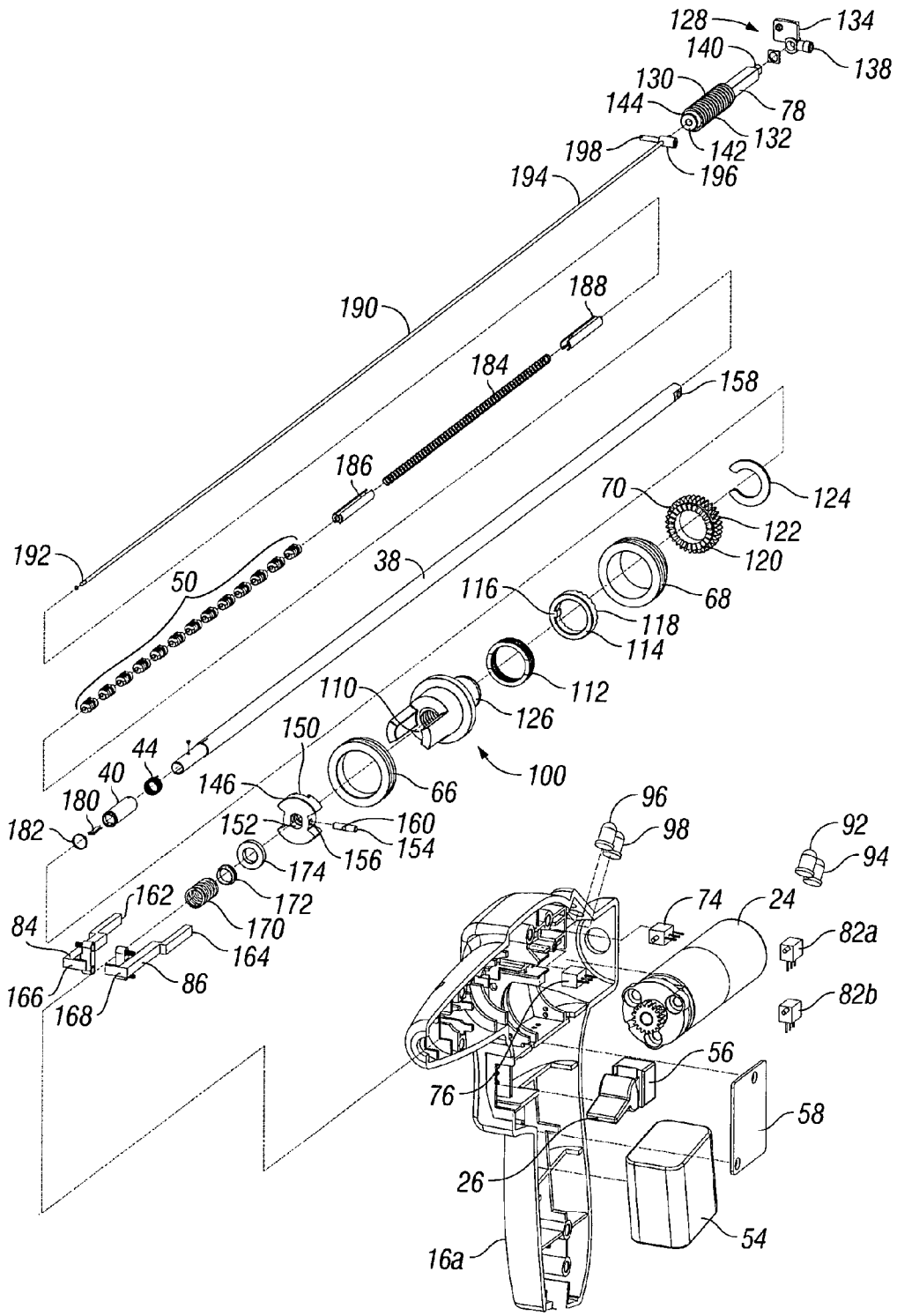
FIG. 4 is a perspective view, with parts separated, of the powered tacker device.

Powered tacker 10 is provided with a safety mechanism or electronic lockout 80 which prevents actuation of powered tacker 10 when powered tacker 10 has not been correctly positioned against tissue. Specifically, electronic lockout 80 prevents actuation of powered tacker 10 until such time as outer tube 30 has been pressed against tissue and moved proximately a predetermined distance relative to handle assembly 12. At least one safety switch 82 (a pair of safety switches 82a are illustrated in FIG. 4) may be provided within handle housing 12. It is envisioned that powered tacker 10 cannot be actuated until at least one safety switch 82 has been activated to indicate that outer tube 30 has been moved proximately a predetermined amount. Further, it is envisioned that for powered tacker 10 to be activated, at least one safety switch 82 is activated, then outer tube 30 travels from the end of the stroke until contact arm 78 contacts distal limit switch 76. Upon release of pressure on outer tube 30, contact arm 78 retracts until proximal limit switch 74 is activated, indicating powered tacker 10 is in its original position.

Figure 6:
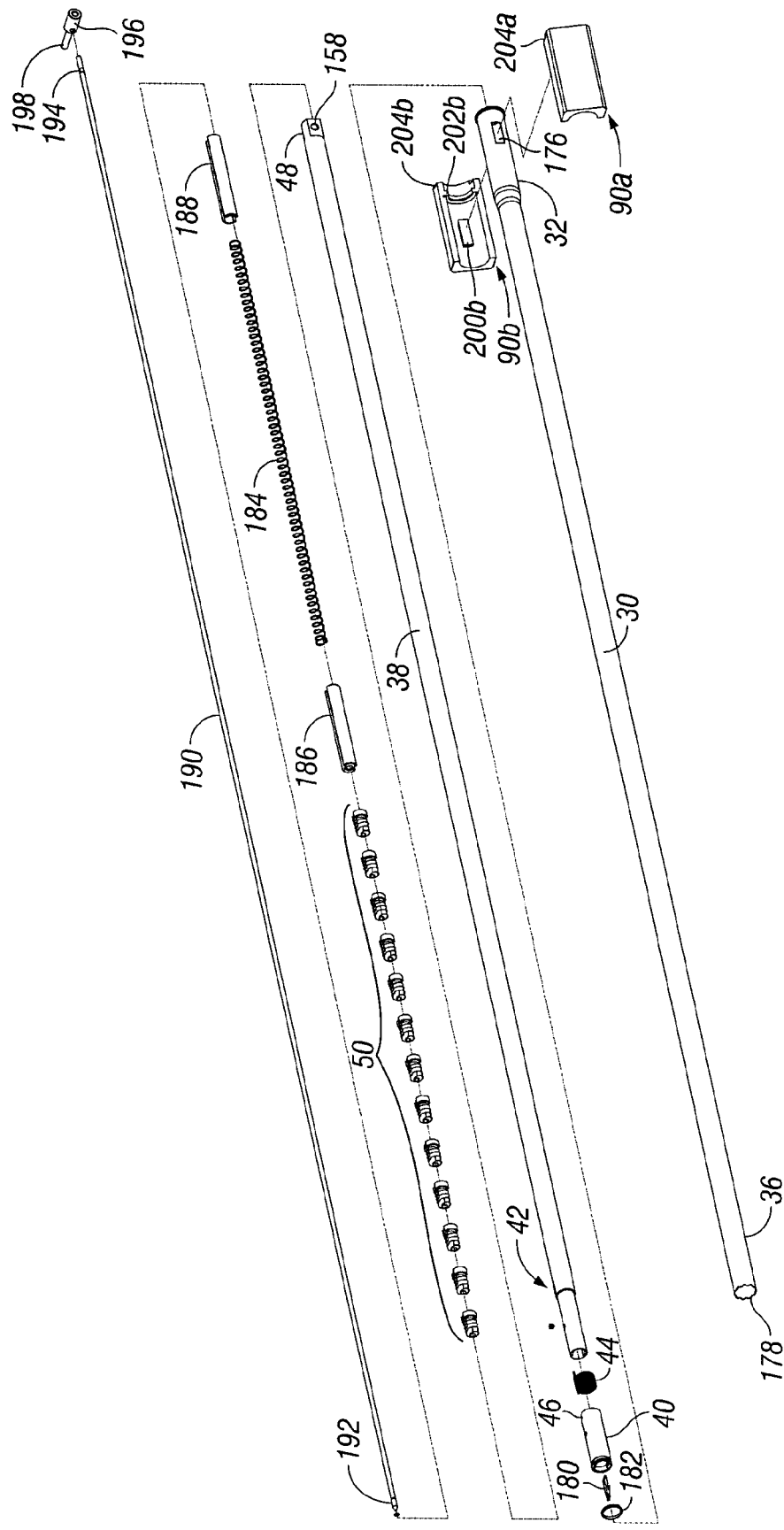
FIG. 6 is a perspective view, with parts separated, of a distal tacker assembly of the powered tacker device.

Electronic lockout 80 includes a first doglegged arm 84 (FIG. 4) and a second doglegged arm 86. Doglegged arms 84 and 86 are supported for longitudinal movement within handle housing 16 by mounting brackets 88. Electronic lockout 80 further includes a base block (FIG. 6 illustrates block halves 90a and 90b) which is engageable with proximal end 32 of outer tube 30, as well as doglegged arms 84 and 86, to actuate safety switches 82a and 82b. Base block may be formed as first and second block halves 90a and 90b which clamp about outer tube 30 in the manner described hereinbelow. Thus, proximal movement of outer tube 30 relative to handle housing 12 actuates safety switches 82a and 82b to permit operation of powered tacker 10.

As noted hereinabove, handle assembly 12 includes an indicator light assembly 28 which is provided to indicate the various operational conditions of powered tacker 10. Indicator light assembly 28 includes four lights provided on body portion 20 of handle housing 16. In this embodiment, the four lights comprise first, second, third, and fourth LED type indicator lights 92, 94, 96 and 98 respectively. First indicator light 92 is green and corresponds to the condition where outer tube 30 has been moved proximately to actuate safety switches 82a and 82b. Second indicator light 94 is red and corresponds to the condition where outer tube 30 is in the initial distal most position prior to engagement with tissue and thus actuation on safety switches 82a and 82b. Likewise, third indicator light 96 corresponds to the initial position of drive assembly 60 where proximal limit switch 74 has been actuated and fourth indicator light 98 corresponds to the final position of drive assembly 60 where distal limit switch 76 has been actuated. In this manner, the operational status and condition of powered tacker 10 at any point during a surgical procedure is visually indicated to the user.

Figure 5:
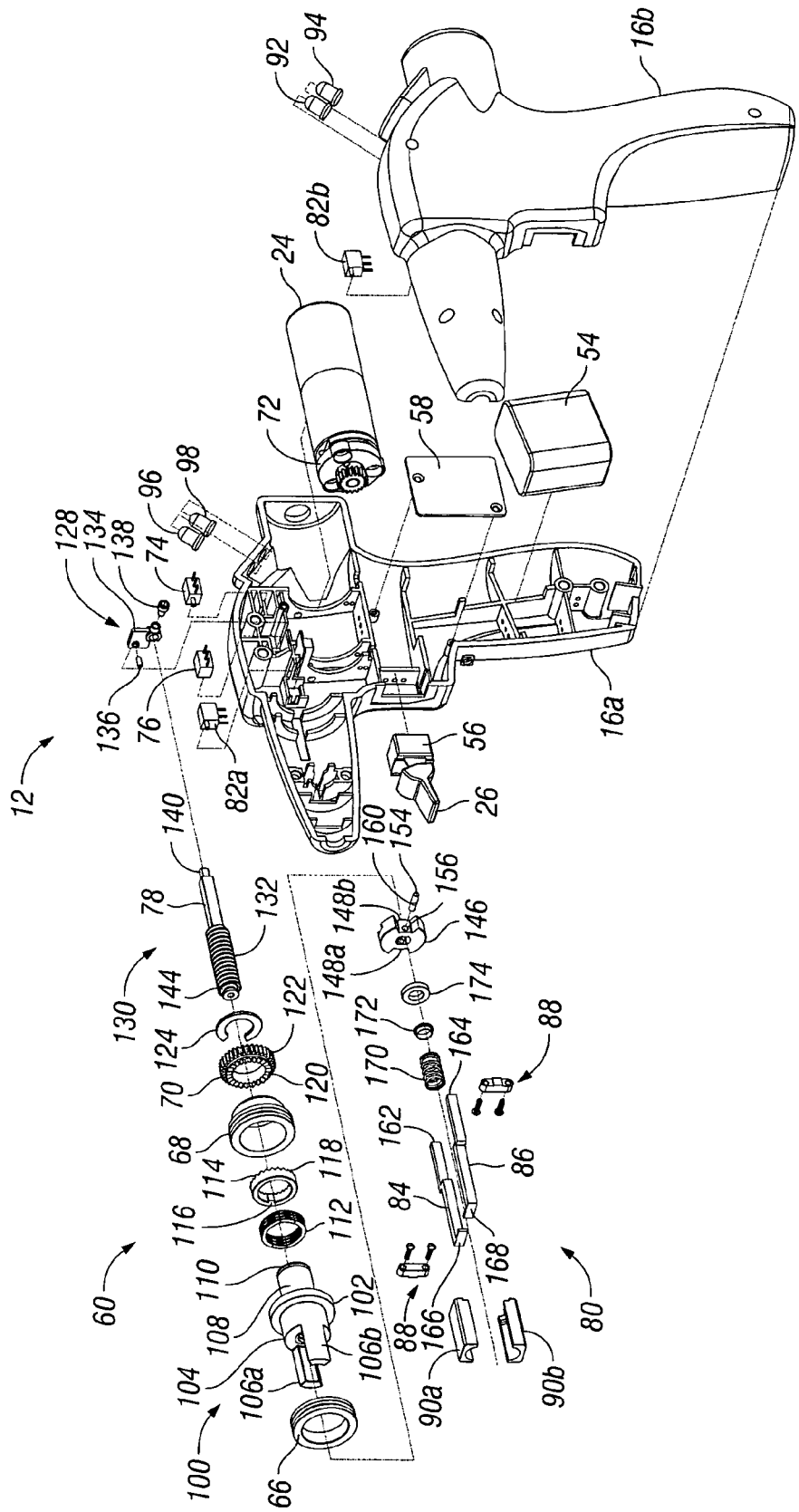
FIG. 5 is a perspective view, with parts separated, of the handle assembly.

Referring now to FIGS. 4 and 5, the various components of drive assembly 60 will now be described. Drive assembly 60 generally includes a keyed journal 100 having a central flange 102. Keyed journal 100 includes a distal hub 104 extending distally from central flange 102. A pair of longitudinally extending distal keys 106a and 106b extend distally from distal hub 104. Distal keys 106a and 106b are provided to rotate inner tube 38 as well as allow inner tube 38 to move longitudinally as keyed journal 100 is rotated. Keyed journal 100 additionally includes a proximal hub 108. Keyed journal 100 is rotatably mounted within handle housing 16. Distal hub 104 is rotatably supported within distal journal 66 while proximal hub 108 is rotatably supported within proximal journal 68. Keyed journal 100 additionally includes a threaded throughbore 110 which enables keyed journal 100 to be rotated within handle assembly 12.

A biasing spring 112 is mounted about proximal hub 108 and is provided to urge a mesh gear 114 into engagement with drive gear 70. Mesh gear 114 includes a key 116 which is configured to engage a longitudinally extending slot (not shown) formed in proximal hub 108. In order to engage mesh gear 114 with drive gear 70, mesh gear 114 includes a plurality of teeth 118 which are engageable with distal teeth 120 formed on drive gear 70. The provision of key 116 within the longitudinally extending slot formed in proximal hub 108 allows mesh gear 114 to rotate keyed journal 100 while at the same time allowing for a limited amount of longitudinal movement of mesh gear 114 relative to keyed journal 100 against the bias of biasing spring 112. Thus, mesh gear 114 may move into and out of engagement with drive gear 70 against the bias of biasing spring 112. This provides protection against a surgical fastener from being over rotated into tissue due to excessive torque provided by drive gear 70 to mesh gear 114.

A C-clip 124 is provided within a proximal groove 126 formed in proximal hub 108 in order to retain biasing spring 112, mesh gear 114 and drive gear 70 on proximal hub 108.

As noted hereinabove, the degree and direction of rotation of inner tube 38 is controlled and limited by proximal and distal limit switches 74 and 76. Limit switches 74 and 76 are turned on and turned off by engagement with contact arm 78. A contact assembly 128 is provided on contact arm 78 to engage limit switches 74 and 76. Contact arms 78 and contact assembly 128 are part of a limit drive bar 130. Limit drive bar 130 is a part of drive assembly 60 and, in addition to moving contact assembly 128 between limit switches 74 and 76, converts rotary motion of keyed journal 100 into longitudinal motion of inner tube 38 relative to handle assembly 12. Limit drive bar 130 includes a threaded distal surface 132 which is engageable with threaded throughbore 110 of keyed journal 100. Thus, as keyed journal 100 is rotated about limit drive bar 130, limit drive bar 130 is moved longitudinally in the distal and proximal directions relative to handle assembly 12.

As shown, contact assembly 128 includes a plate 134 having a pin 136 which is engageable with limit switches 74 and 76. Plate 134 is affixed by means of a screw 138 to a proximal end 140 of contact arm 78. Limit drive bar 130 additionally includes a throughbore 142 for passage of a needle associated with powered tacker 10 as described in more detail hereinbelow. Limit drive bar 130 further includes a generally round, distally extending circumferential projection 144 which is provided to move inner tube 38 longitudinally in response to longitudinal motion of limit drive bar 130 as well as allowing inner tube 38 to rotate relative to limit drive bar 130.

In order to transfer the rotational motion of keyed journal 100 and the longitudinal motion of limit drive bar 130 to inner tube 38, drive assembly 60 is provided with a rotator 146. Rotator 146 includes a pair of side slots 148a and 148b which are configured to engage and move along distal keys 106a and 106b of keyed journal 100. Additionally, the engagement of distal keys 106a and 106b with side slots 148a and 148b allows keyed journal 100 to rotate rotator 146. Rotator 146 includes a proximal slot 150 for receipt of circumferential projection 144 of limit drive bar 130. Circumferential projection 144 is free to rotate within proximal slot 150 so that limit drive bar 130 can move rotator 146 longitudinally within handle assembly 12 and still allow rotator 146 to rotate in response to rotation of keyed journal 100.

Rotator 146 includes a center hole 152 for receipt of proximal end 48 of inner tube 38. A pin 154 secures rotator 146 to inner tube 38. Specifically, rotator 146 includes a side hole 158 while proximal end 48 of inner tube 38 includes a side hole 158 for receipt of pin 154 therethrough. Pin 154 additionally includes a pin hole 160 receipt therethrough of a needle as described in more detail hereinbelow. (See also FIG. 7).

As noted hereinabove, electric lockout 80 includes a pair of first and second doglegged arms 84 and 86. Doglegged arms 84 and 86 include respective proximal ends 162 and 164 which are engageable with safety switches 82a and 82b. Additionally, doglegged arms 84 and 86 include respective distal ends 166 and 168 which are configured to engage base block 90. In order to bias base block 90, and thus outer tube 30 in an initial distal direction, electronic lockout 80 includes a biasing spring 170 having a proximal spring guide 172. Biasing spring 170 is positioned between spring guide 172 and base block 90. A bushing 174 supports spring guide 172 within handle housing 16. Thus, as outer tube 30 is moved proximally against the bias of biasing spring 170, proximal ends 162 and 164 of doglegged arms 84 and 86 engage safety switches 82a and 82b to allow powered tacker 10 to be actuated.

Referring now to FIGS. 4 and 6, the details of distal tacker assembly 14 will now be described. As noted hereinabove, outer tube 30 is mounted for longitudinal movement relative to handle assembly 12. Outer tube 30 includes a longitudinal slot 176 near proximal end 32 for engagement with base block 90 as described in more detail hereinbelow (see FIG. 7). A plurality of circumferential crenellations 178 are formed all on distal end 36 of the outer tube 30. Crenellations 178 assist in securing a prosthetic mesh in position against tissue and preventing the prosthetic mesh from rotating as powered tacker 10 rotates fastener 50 therethrough.

Distal tacker assembly 14 further includes a bottom guide 180 which is provided to facilitate the transfer is of fasteners 50 from within inner tube 38 and into driver 42 a position to be engaged with driver 40. A friction ring 182 is provided on driver 40 and is configured to engage an interior of outer tube 30 to allow inner tubes 38 to initially rotate a predetermined distance prior to rotating driver 40 in a manner described in more detail hereinbelow.

As noted hereinabove, distal tacker assembly 14 contains a plurality of fasteners 50. Fasteners 50 are contained within an interior of inner tube 38 which acts as a fastener cartridge. In order to move the plurality of fasteners 50 towards driver 40, a spring 184 is provided within an interior of inner tube 38. A distal spring guide 186 is provided between spring 184 and fasteners 50 and a proximal spring guide 188 is provided between spring 184 and proximal end 48 of inner tube 38.

As indicated hereinabove, powered tacker 10 includes an elongate needle 190 which extends from handle assembly 12 through distal tacker assembly 14. Needle 190 is provided with a distal penetrating tip 192. Needle 190 extends through fasteners 50 in a manner described in more detail below. Penetrating tip 192 is provided to make an initial, or pilot, hole in mesh and/or tissue for installation of fasteners 50. A proximal end 194 of needle 90 is affixed to handle housing 12 by means of a bushing 196 which has a pin 198 engageable with handle housing halve 16a. Thus, needle 190 is affixed to, and remains stationary relative to, handle assembly 12.

Referring now to FIG. 6, and as noted hereinabove, proximal end 32 of outer tube 30 is affixed to base block 90. Specifically, base block 90 includes a pair of inward projections 200a and 200b (inward projection 200a is hidden from view in FIG. 6) which each engage proximal slot 176 (only a single slot 176 is visible in FIG. 6) in outer tube 30. Base block 90 further includes a circumferential flange 202 formed as flange halves 202a (hidden from view in FIG. 6) and 202b which are configured to engage in secure biasing spring 170 (FIG. 7) within handle assembly 12. Base block 90 further includes a pair of proximal detents 204a and 204b which are configured to engage and move distal ends 166 and 168 of doglegged arms 84 and 86. In the embodiment illustrated in FIG. 7, side hole 158 of inner tube 38 is disposed on a substantially flat portion 49 adjacent proximal end 48 thereof. Flat portion 49 is included on both sides of inner tube 38, such that inner tube 38 may be oriented with rotator 146 and locked via pin 154, as discussed above.

Figure 7:
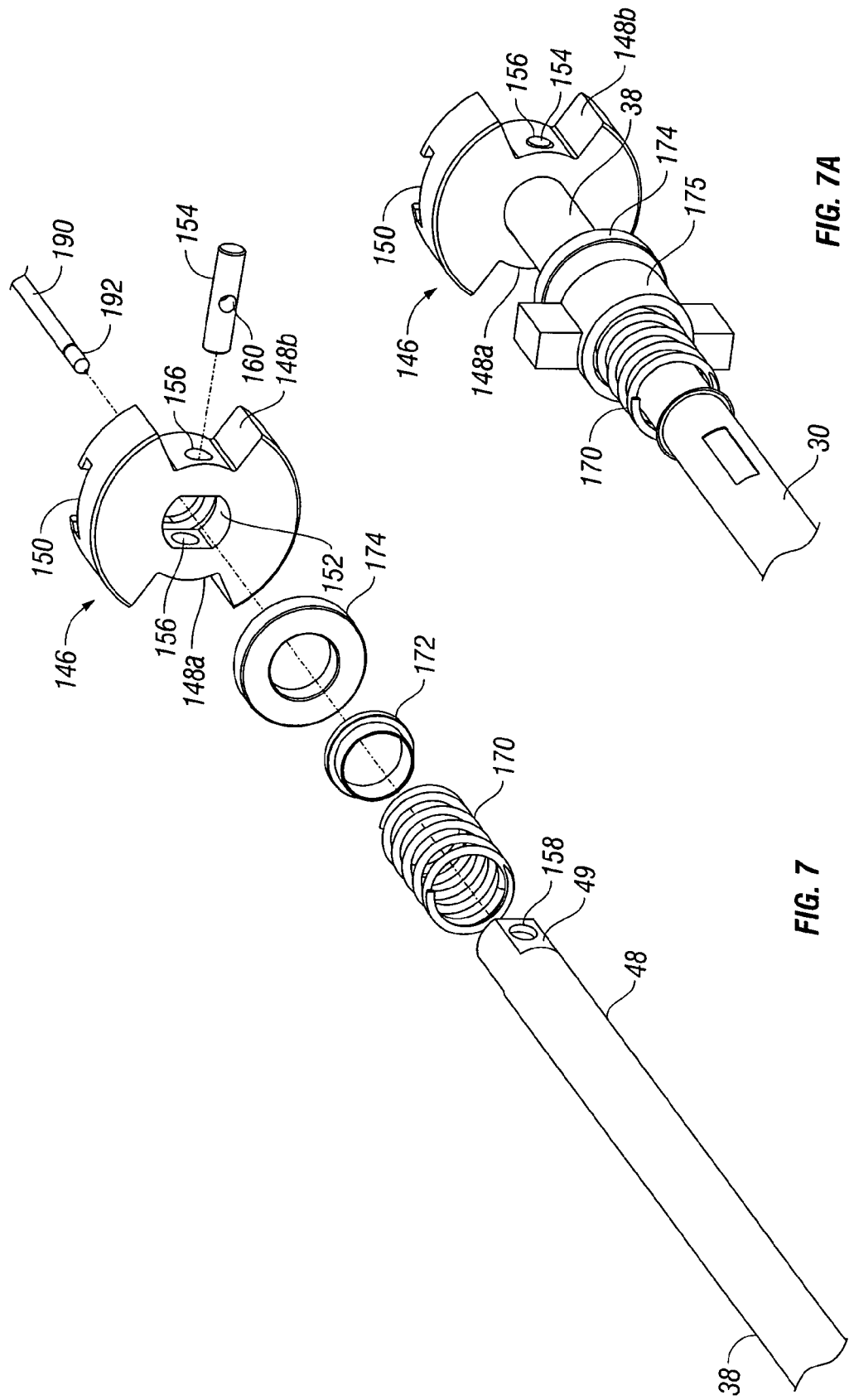
FIG. 7 is a perspective view, with parts separated, of components contained within a nose cone portion of the handle assembly.

With reference to FIG. 7A, a partially exploded view of several elements illustrated in FIG. 7 is shown. Here, a spring retainer 175 is illustrated in place of spring guide 172 of FIG. 7. It is envisioned that spring retainer 175 may be used without or in addition to spring guide 172 and/or bushing 174. Additionally, outer tube 30 is shown positioned adjacent spring 170 and covering a portion of inner tube 38.

Figure 8:
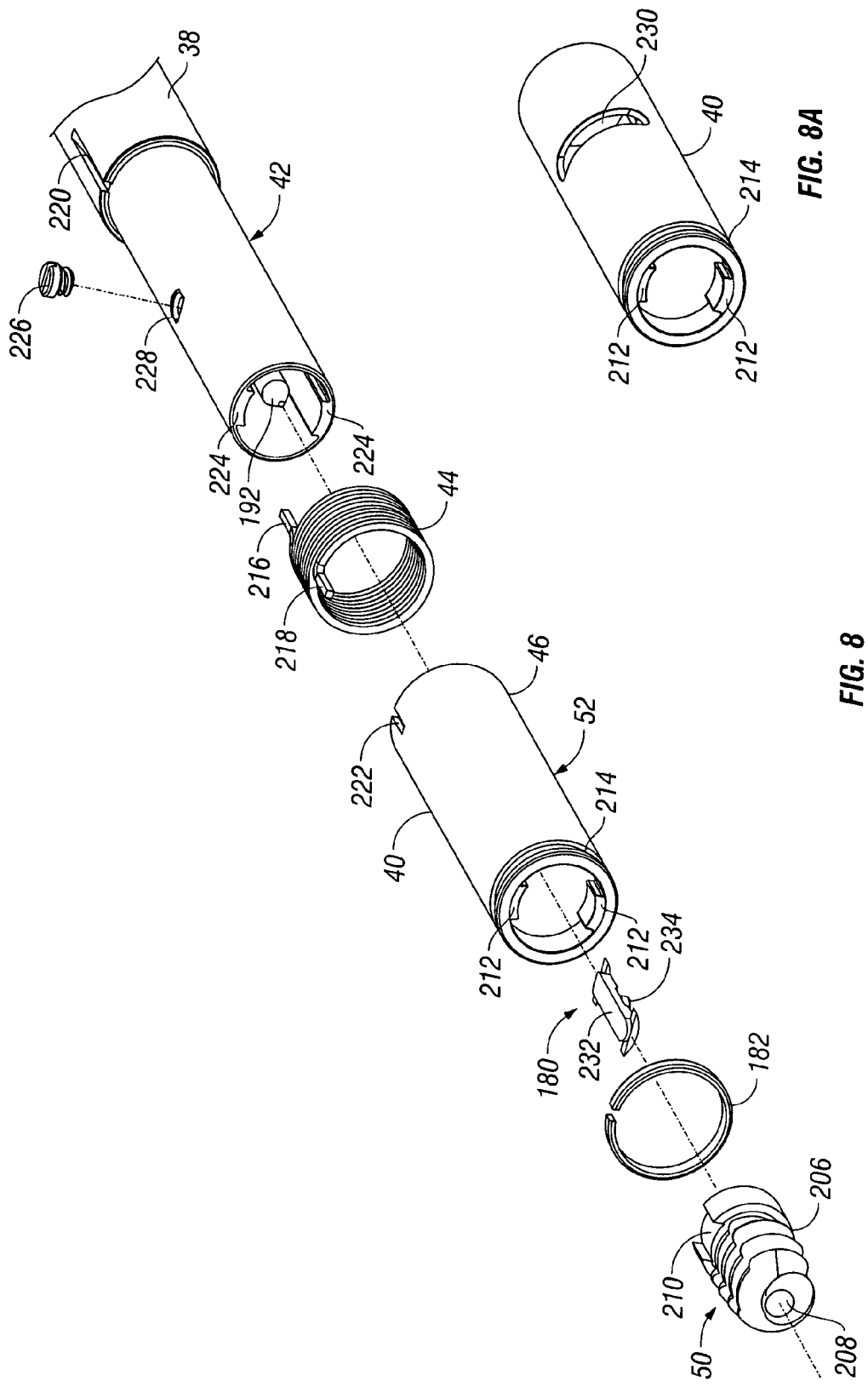
FIG. 8 is a perspective view, with parts separated, of distal end components of the distal tacker assembly.

Referring to FIG. 8, the details of the distal end of distal tacker assembly 14 will now be described. As noted hereinabove, distal tacker assembly 14 is configured to install a surgical fastener 50 into tissue. Surgical fasteners 50 are of the type disclosed in U.S. patent application Ser. No. 10/560,879, filed on Dec. 13, 2005, the contents of which are incorporated herein by reference. Fastener 50 includes an outer helical thread 206 for rotation into tissue. Fastener 50 additionally includes a throughbore 208 for receipt of tissue penetrating tip 192 of needle 190. As noted hereinabove, fastener 50 is driven into tissue by means of driver 40. Thus fastener 50 includes a slotted head to tend which is configured to be engaged by drive tabs 212 formed in distal end 52 of driver 40. Driver 40 includes a distal circumferential groove 214 for receipt of friction ring 182.

Driver 40 is mounted on inner tube 38 by inserting driver 40 over stepped down distal end 42 of inner tube 38. As noted hereinabove, a spring 44 is provided between driver 40 and inner tube 38. Spring 44 includes a proximal spring end 216 and a distal spring end 218. Spring 44 allows inner tube 38 to rotate an initial predetermined amount relative to driver 40 against the bias of spring 44. Proximal end 216 of spring 44 is affixed within a slot 220 in inner tube 38 while a distal end 218 of spring 44 is affixed within a driver slot 222 formed in driver 40. Inner tube 38 is provided with a pair of longitudinally extending transfer bars 224 which extends substantially along the length of inner tube 38. In an initial position, transfer bars 224 are in longitudinal alignment with drive tabs 212 formed in driver 40. Initial rotation of inner tube 38 relative to driver 40 rotates transfer bars 222 out of alignment with drive tabs 212.

As discussed, inner tube 38 is capable of an initial limited amount of rotation relative to driver 40 before inner tube 38 begins to rotate driver 40. Inner tube 38 includes a set screw 226 which extends through a hole 228 provided in distal end 42 of inner tube 38. Referring for the moment to FIG. 8A, driver 40 includes an index slot 230 which is configured to receive set screw 226 and allow inner tube 38 to rotate a predetermined distance before set screw 226 engages an edge of slot 230 to rotate driver 40 along with inner tube 38. This allows driver 40 to rotate and install a fastener 50 into tissue while preventing subsequent fasteners 50 from moving along transfer bars 224 and into driver 40.

As noted hereinabove, distal tacker assembly 14 further includes a bottom guide 180 which assists in transferring fasteners 50 from inner tube 38 and into driver 40. Bottom guide 180 includes a guide rail 232 and a guide pin 234. Bottom guide 180 is mounted within a slot (not shown) formed in driver 40 while guide pin 234 extends through a hole (not shown) formed in proximal end 48 of inner tube 38.

Figure 9:
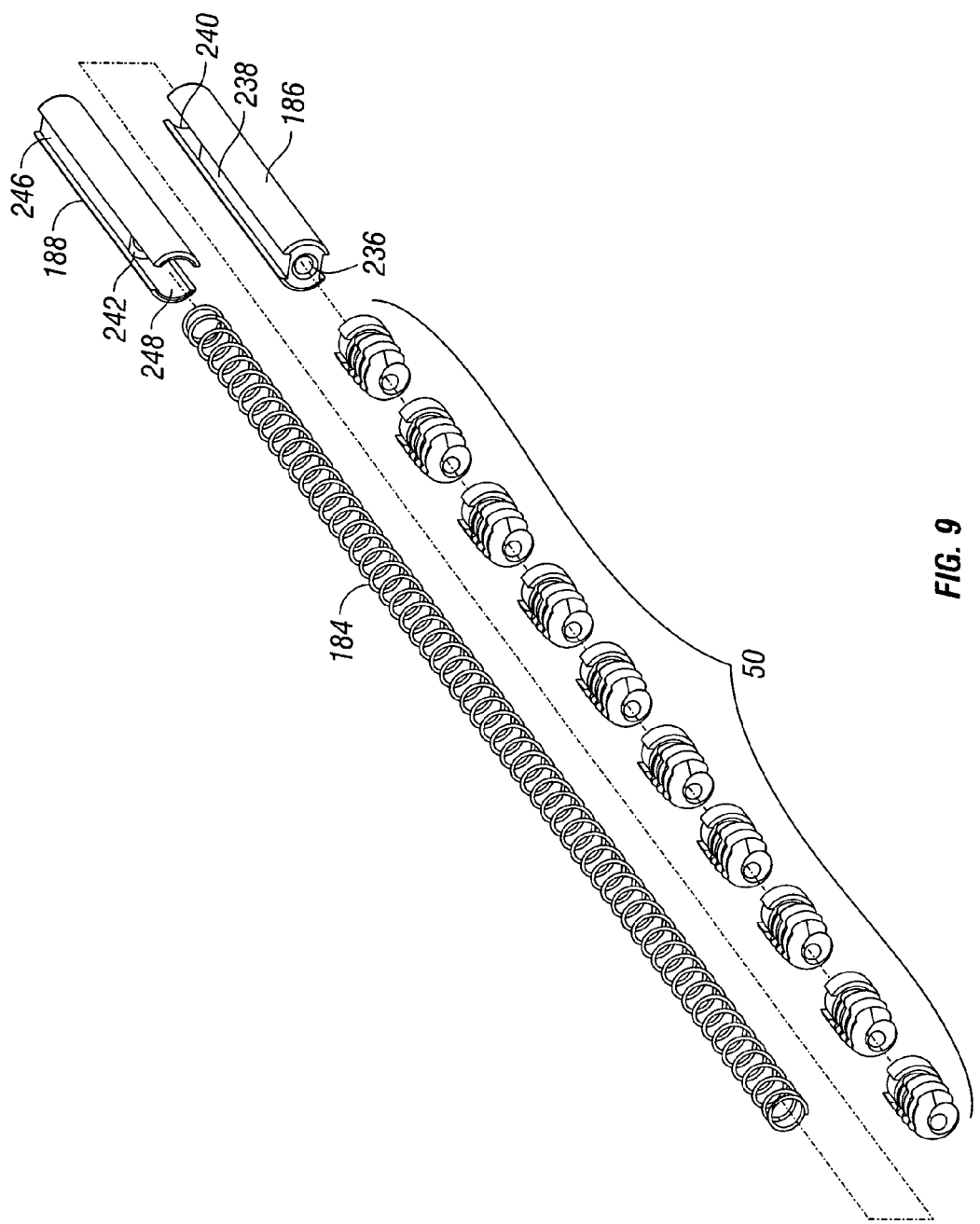
FIG. 9 is a perspective view, with parts separated, of fasteners and a biasing spring assembly associated with a central portion of the distal tacker assembly.

Referring now to FIG. 9, as discussed hereinabove, distal tacker assembly 14 includes spring 184 to bias a plurality of fasteners 50 distally within inner tube 38. Distal spring guide 186 includes a throughbore 236 for receipt of needle 190 therethrough. Distal spring guide 186 further includes a pair of longitudinally extending slots 238 which are configured to ride along transfer bars 224 are formed in inner tube 38. A recess 240 is provided in distal spring guide 186 to capture spring 184. Similarly, proximal spring guide 188 includes a throughbore 248 and longitudinally extending slots 246. Proximal spring guide 188 additionally includes a recess 248 to capture and stabilize spring 184 within inner tube 38. Engagement of slots 238 and 246 in distal spring guides 186 and 188, respectively, with transfer bars 224 ensure that fasteners 50 remain in proper alignment to be transferred into driver 40.

Figure 10:
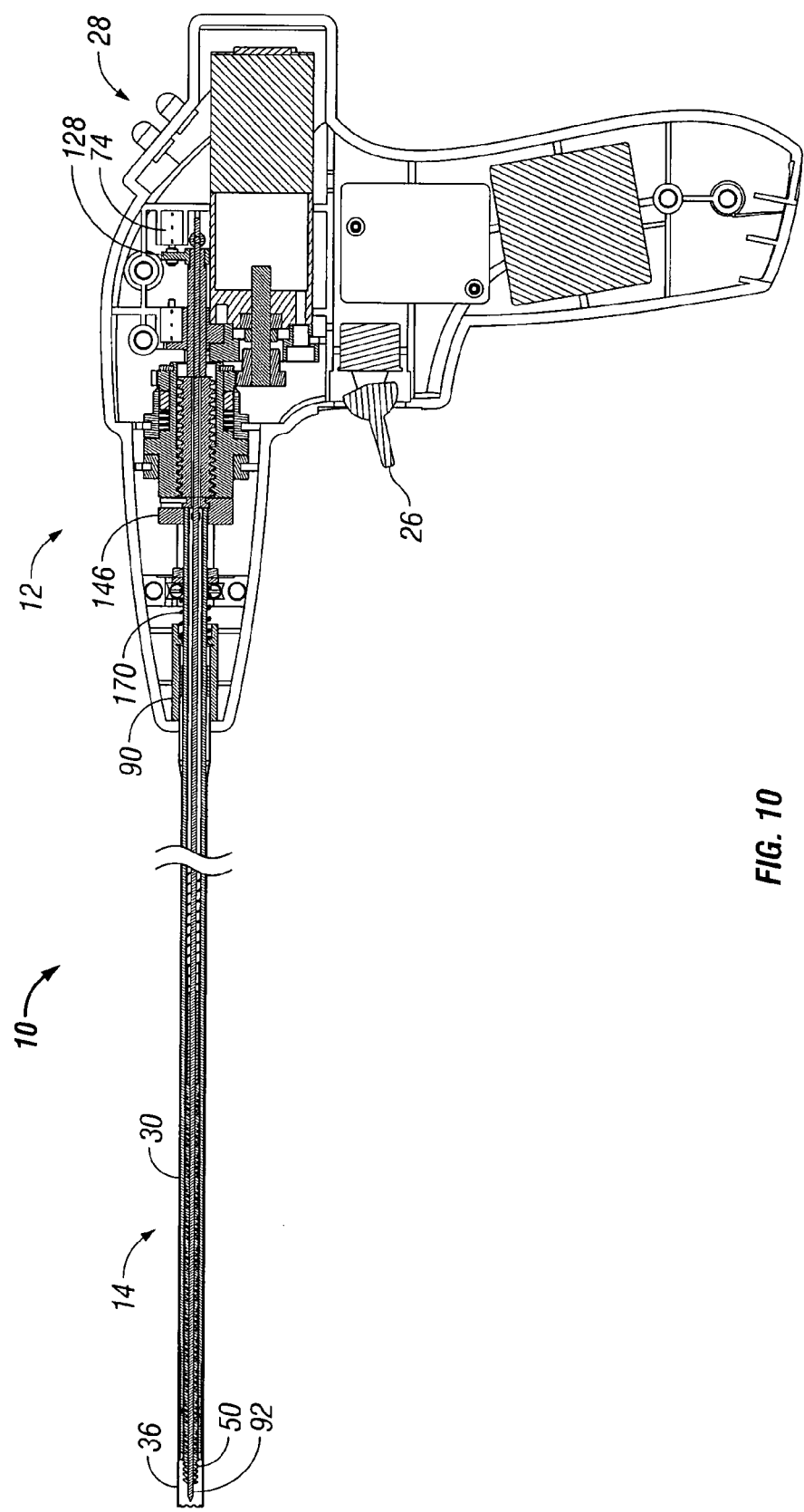
FIG. 10 is a side view, shown in section, of the powered tacker device.

Referring now to FIGS. 10-18, and initially with regard to FIG. 10, the use of powered tacker 10 to install surgical fastener 50 through prosthetic match and into tissue will now be described. In the initial position, distal end 36 of outer tube 30 is in the distal most position shielding tissue penetrating tip 92 of needle 90 and fastener 50. Base block 90 is also in a distal most position against the bias of spring 170. Referring for the moment back to FIG. 2, doglegged arm 86 is also in a distal most position remote from the safety switch 82. As noted hereinabove, safety switch 82 prevents actuation of powered tacker 10 until outer tube 30 has been properly positioned against tissue.

Trigger 26 is in the unactuated position and contact assembly 128 is engaged with proximal limit switch 74. As noted hereinabove, actuation of proximal limit switch 74 triggers one of the LEDs in indicate light assembly 28 to signify to the user that powered tacker 10 is ready for use.

Figure 11:
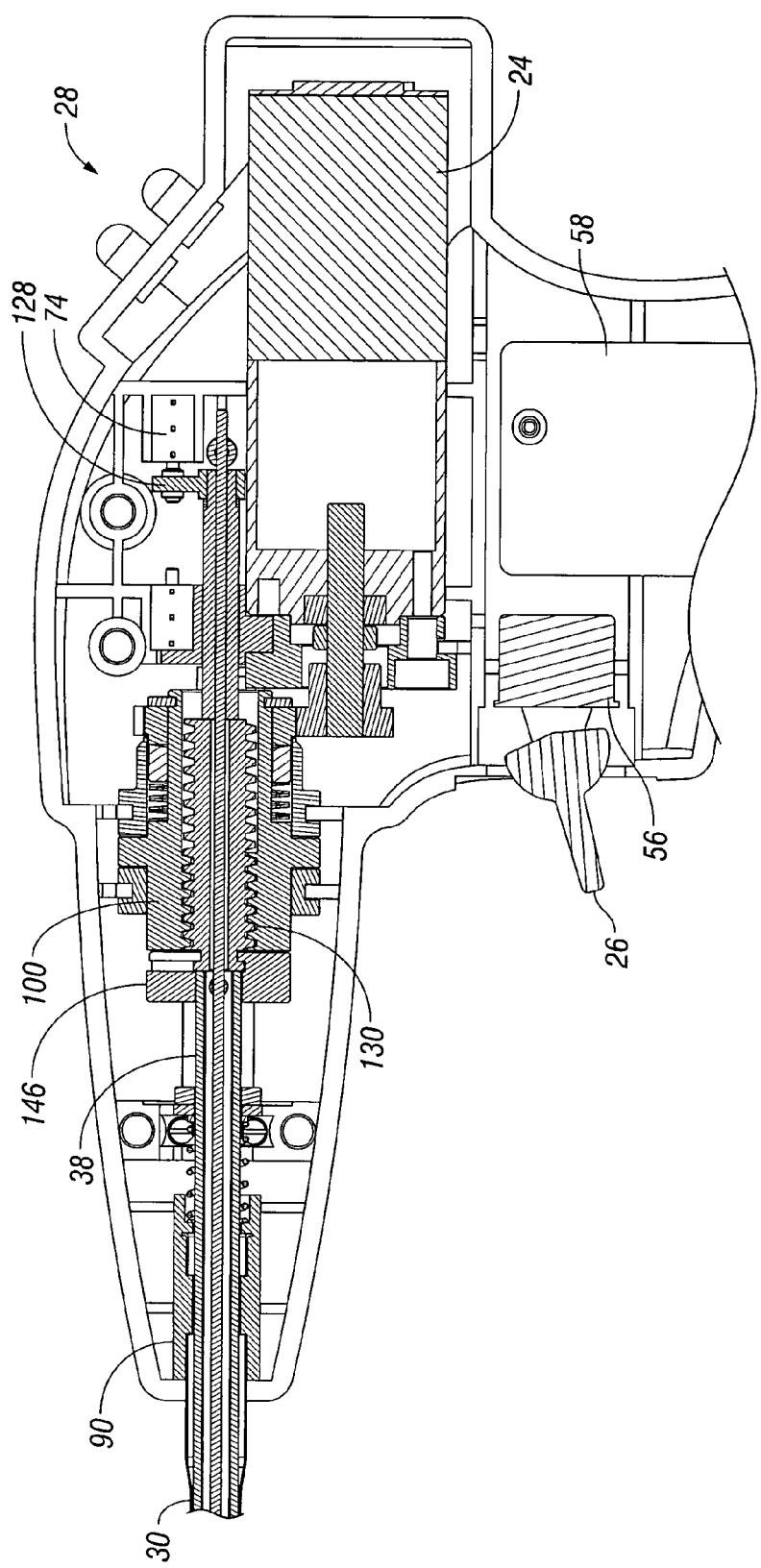
FIG. 11 is a partial side view, shown in section, of the handle assembly prior to actuation.
Figure 12:
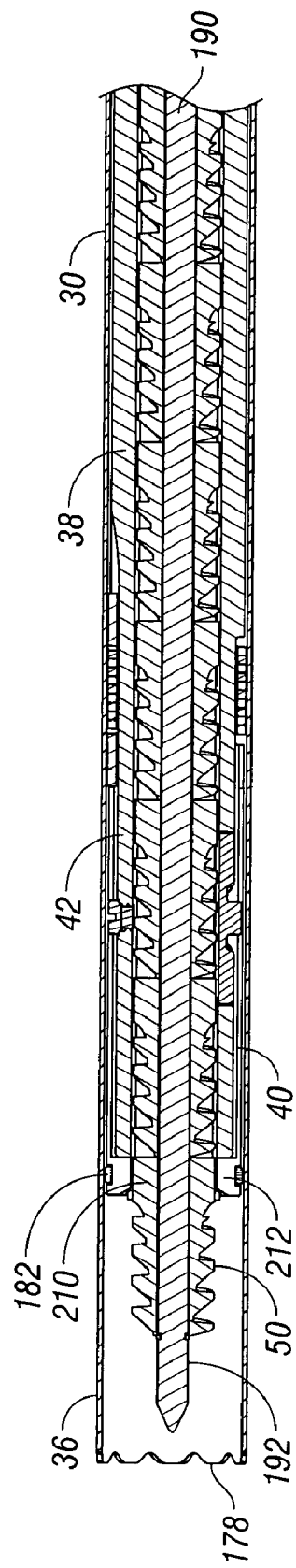
FIG. 12 is an enlarged side view, shown in section, of the distal portion of the distal tacker assembly immediately prior to use.

As best shown in FIG. 11, rotator 146 and limit drive bar 130 are in a proximal most position relative to keyed journal 100. In this position, inner tube 38 is also in a proximal most position. As shown in FIG. 12, drive tabs 212 of driver 40 are engaged with slotted head 210 of fastener 50.

Figure 13:
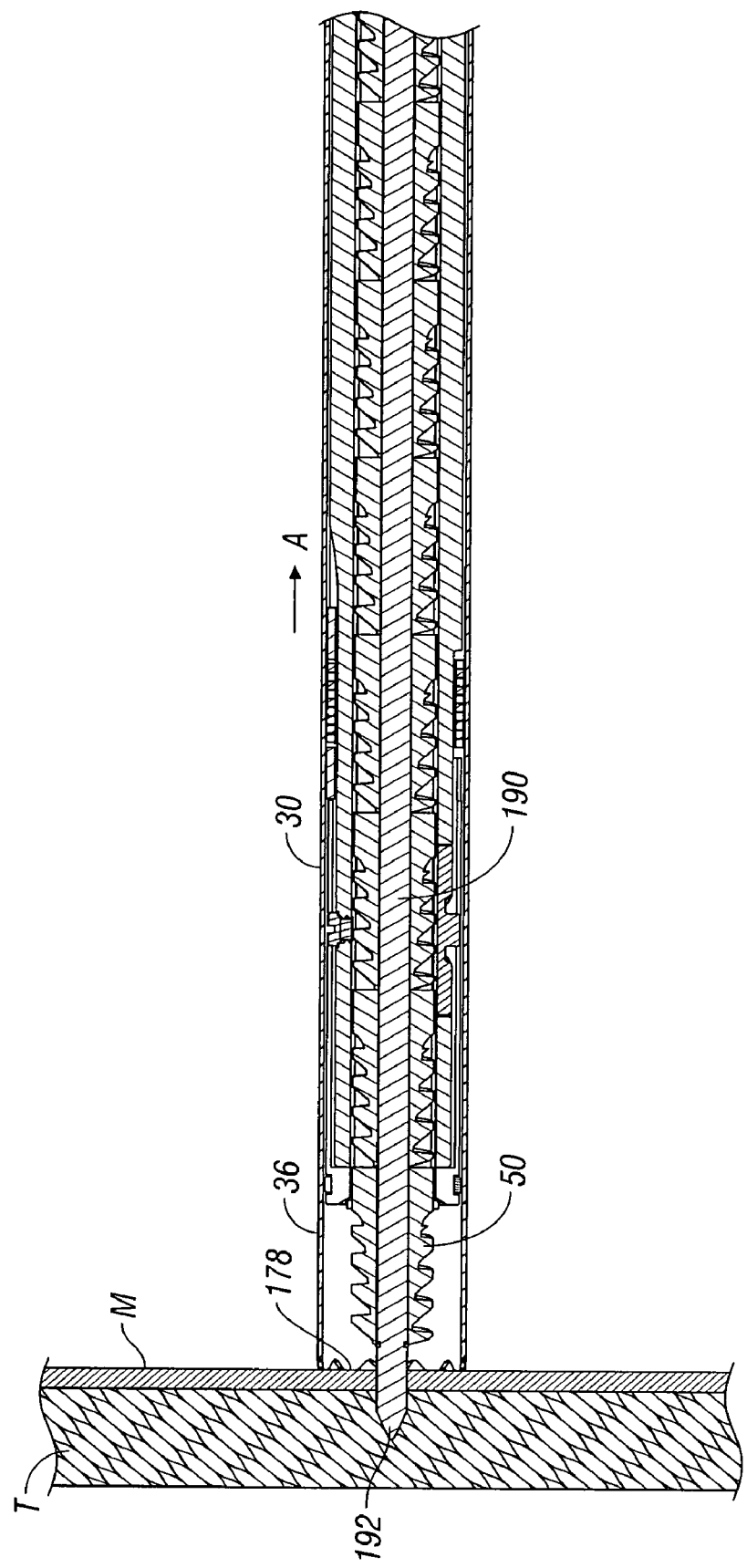
FIG. 13 is an enlarged side view, shown in section, of the distal portion of the distal tacker assembly being urged against prosthetic mesh and tissue.

Referring to FIG. 13, to attach a prosthetic mesh M to tissue T, distal end 36 of outer tube 30 is urged against mesh M and tissue T causing tissue penetrating tip 192 of needle 190 to penetrate through mesh M and into tissue T. Crenellations 178 provided on distal end 36 of outer tube 30 secure and stabilize mesh M as fastener 50 is subsequently rotated therethrough. As shown, this biases outer tubes 30 proximally in the direction of arrow A.

Figure 14:
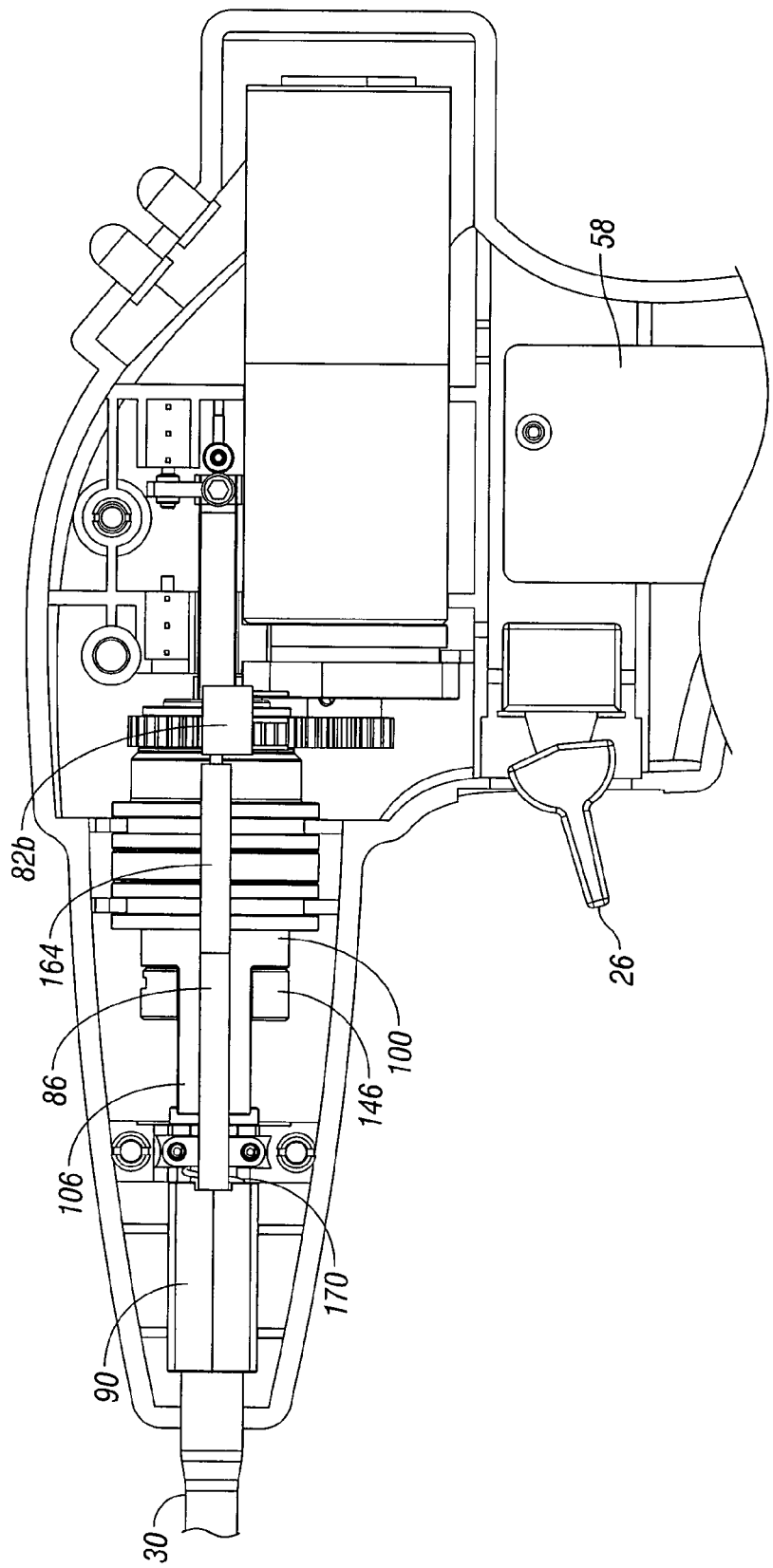
FIG. 14 is a partial side view, with half the handle housing removed, of the handle assembly during actuation of a safety mechanism.

As best shown in FIG. 14, as outer tube 30 is biased proximally, outer tube 30 moves base block 90 proximally against the bias of spring 170. Proximal movement of base block 90 moves doglegged arm 86, and specifically proximal end 164 of doglegged arm 86, against safety switch 82b to actuate switch 82b. Once switch 82b has been actuated, it signals circuit board 58 that powered tacker 10 has been properly positioned and it is safe to actuate powered tacker 10.

Figure 15:
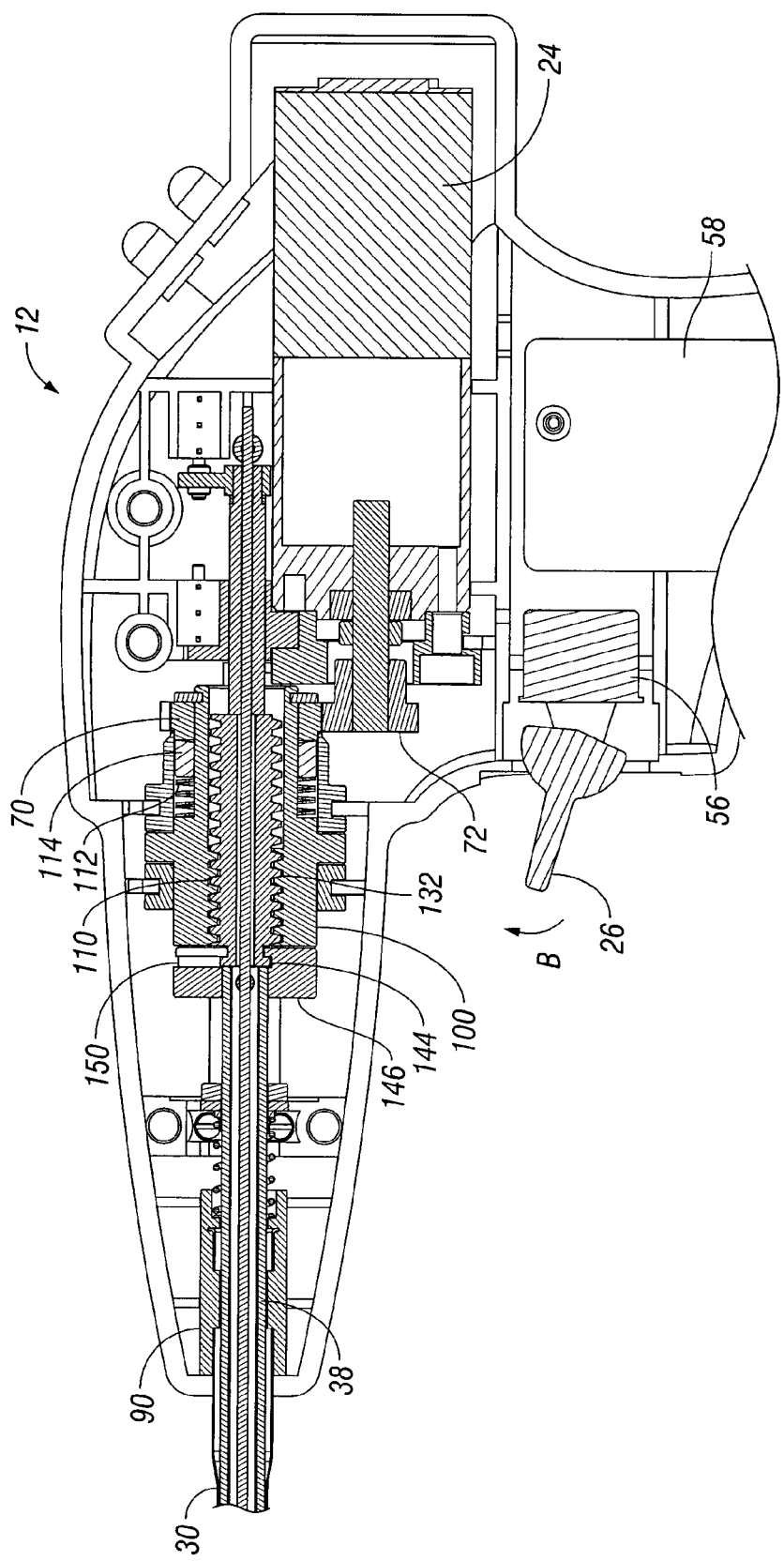
FIG. 15 is a partial side view, shown in section, of the handle assembly during an initial actuation.

Referring now to FIG. 15, once powered tacker 10 has been properly positioned, trigger 24 may be actuated in the direction of arrow B to cause circuit board 58 to turn on motor 24. Once motor 24 has been actuated it rotates worm gear 72 which in turn rotates drive gear 70. Rotation of drive gear 70 rotates mesh gear 114 and keyed journal 100 to initiate rotation and translation of inner tube 38 relative to handle assembly 12. As noted hereinabove, should anything restrict the motion of inner tube 38, mesh gear 114 can compress against the bias of spring 112 and thereby disengage distal tacker 14 from handle assembly 12. Rotation of keyed journal 100 causes threaded inner surface 110 to move limit drive bar 130 in response to engagement of threaded inner surface 110 with threads 132 of limit drive bar 130. Engagement of distal projection 144 of limit drive bar 130 within the slot 150 of rotator 146 causes distal longitudinal motion of rotator 146. As rotator 146 moves distally it moves inner tube 38 distally.

As noted hereinabove, rotation of keyed journal 100 also causes rotation of rotator 146. Additionally, rotator 146 can move longitudinally along distal keys 106 of keyed journal 100. Thus, keyed journal 100 servers the dual purpose of rotating rotator 146, and thus inner tube 38, as well as allowing for distal motion of rotator 146 relative to keyed journal 100.

Figure 16:
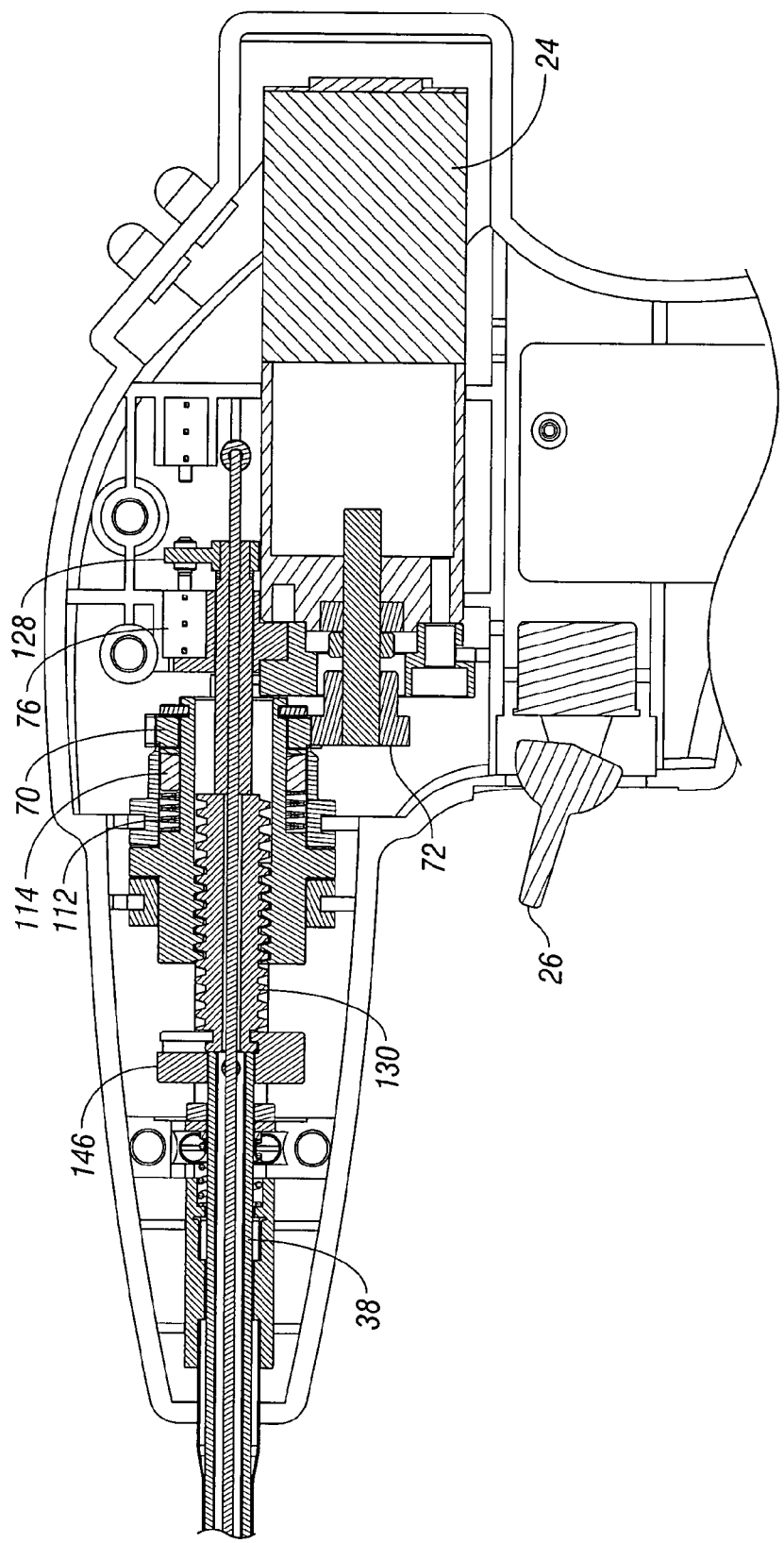
FIG. 16 is a partial side view, shown in section, of the handle assembly in the actuated position.

Referring now to FIG. 16, once limit drive bar 130 has been moved to its distal most position, contact assembly 128 engages distal limit switch 76 to turn off motor at 24 and prevent any over rotation of inner tube 38.

Figure 17:
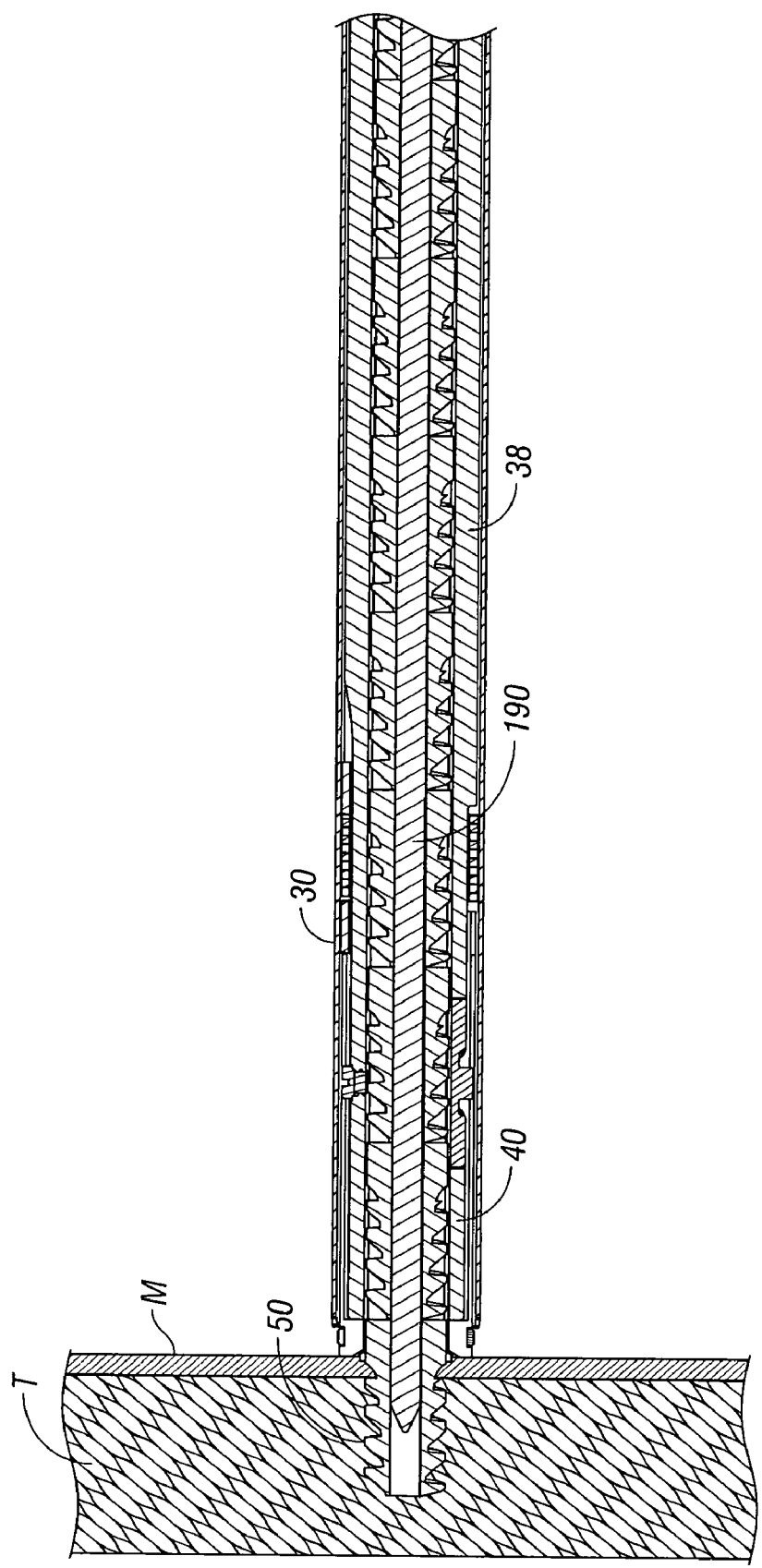
FIG. 17 is an enlarged side view, shown in section, of the distal portion of the distal tacker assembly during actuation to install a surgical fastener through prosthetic mesh and into tissue.

As best shown in FIG. 17, full distal movement and rotation of inner tube 38 causes driver 40 to advance and rotate fastener 50 through prosthetic mesh M and into tissue T to thereby secure prosthetic mesh M to tissue T.

While not specifically shown, once a first fastener 50 has been properly installed, trigger 26 can be moved to reverse the rotation of motor 24. Reverse rotation of motor 24 causes reverse rotation of keyed journal 100 thereby moving inner tube 38 proximally to an initial position. As inner tube 38 is rotated in the reverse direction it causes set screw 226 to rotate back through slot 230 in driver 42 an initial position. In the initial position, transfer bars 224 are in alignment with drive tabs 212 so that a subsequent fastener can be transferred into driver 40. Once inner tube 38 is moved back to its initial position, contact assembly 128 contacts proximal limit switch 76 to indicate to the user powered tacker 10 is in condition for subsequent use. As powered tacker 10 is moved away from tissue, outer tube 30 moves back to a distal most position shielding the next subsequent fastener 50 to be installed. When outer tube 30 is in the distal most position safety switch 82 is deactivated preventing powered tacker 10 from operation until outer tube 30 has been again properly positioned against tissue and safety switch 82 is actuated.

Before pressure is applied to powered tacker 10, transfer bars 224 are in alignment with drive tabs 212 and distal end of fastener 50 is contacting a retention feature 191 (FIG. 19) on needle 190. Retention feature 191 prevents fastener 50 in contact therewith from being pushed off needle 190 by spring 184. It is envisioned that when safety switch 82 is engaged, transfer bars 224 rotate clockwise, such that after the initial 90 degree rotation of transfer bars 224, transfer bars 224 and drive tabs 212 are diametrically opposed. It is envisioned that transfer bars 224 and drive tabs 212 remain diametrically opposed for the remainder of the stroke. Here, transfer bars 224 may create the force necessary to push fastener 50 distally and drive tabs 212 are capable of maintaining the frictional fit with head 210 of fastener 50.

Upon completion of the firing stroke, the pressure of powered tacker 10 is released and powered tacker 10 moved proximally—away from ejected fastener 50. Torsion spring 44 may then bring drive tabs 212 back to their resting position, such that drive tabs 212 are substantially aligned with transfer bars 224. Once drive tabs 212 and transfer bars 224 are aligned, spring 184 pushes the next fastener 50 distally until distal portion of fastener 50 contacts retention feature 191 of needle.

Figure 18:
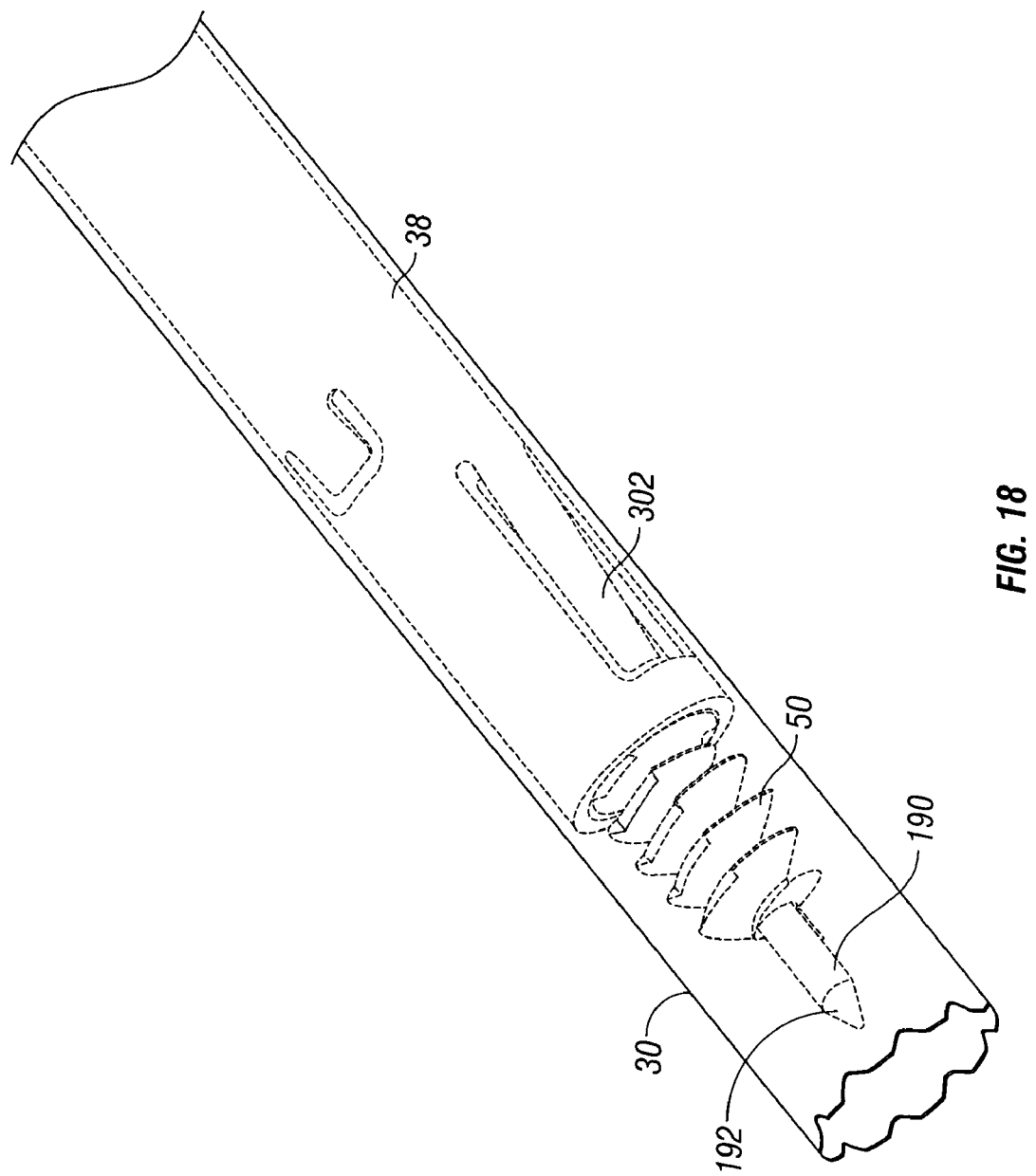
FIG. 18 is an enlarged perspective view of a distal portion of the powered tacker device in accordance with an embodiment of the present disclosure.
Figure 19:
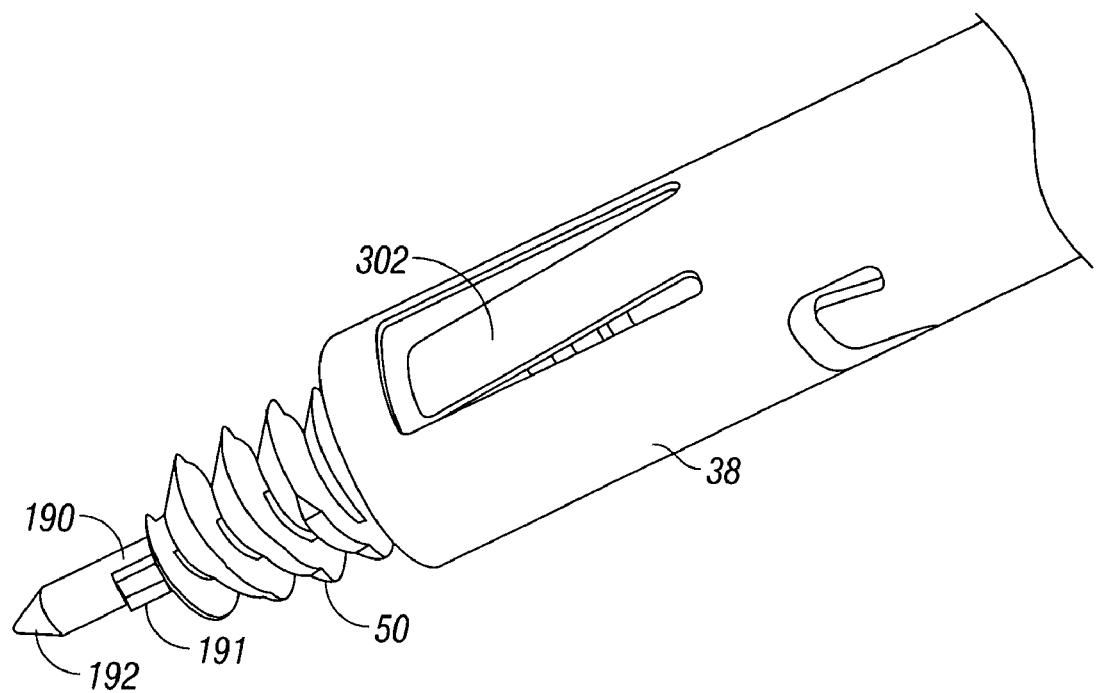
FIG. 19 is an enlarged perspective view of the powered tacker device of FIG. 18 illustrated without the outer tube.
Figure 20:
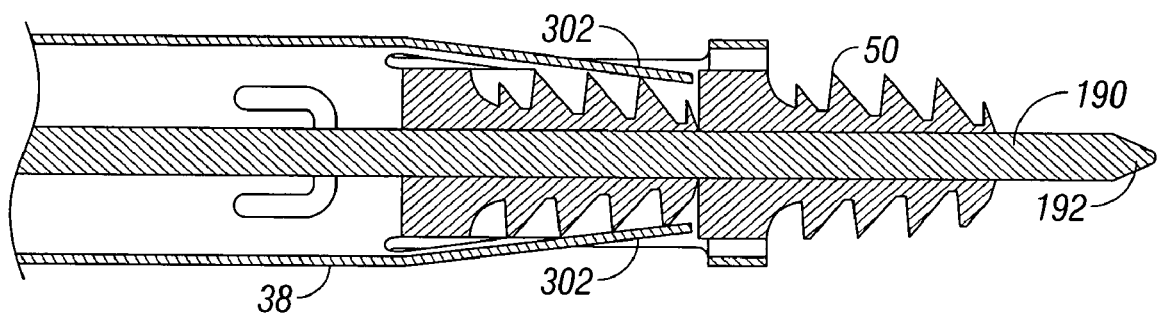
FIG. 20 is a cross-section view of the distal portion of the powered tacker of FIG. 19.

An embodiment of the present disclosure is illustrated in FIGS. 18-20. In this embodiment, inner tube 38 includes at least one tab 302 (two tabs 302 are shown in FIG. 20) and needle 190 includes a retention feature 191 (FIG. 19) proximal of distal penetrating tip 192. Retention feature 191 opposes the force exerted by spring 184, such that fastener 50 does not prematurely become ejected from powered tacker 10. To force fastener 50 past retention feature 191, tabs 302 on inner tube 38 are deflected inwardly such that tabs 302 are disposed proximal of distal-most fastener 50 (see FIG. 20) and inner tube 38 is moved distally. Thus, tabs 302 of inner tube 38 contact a proximal portion of fastener 50 and force fastener to move past retention feature 191 and distally toward tissue. It is envisioned that tabs 302 are biased inwardly. It is also envisioned that tabs 302 are deflected inwardly after contacting a fluted section (not explicitly shown in this embodiment) of outer tube 30 (FIG. 18).

Figure 21:
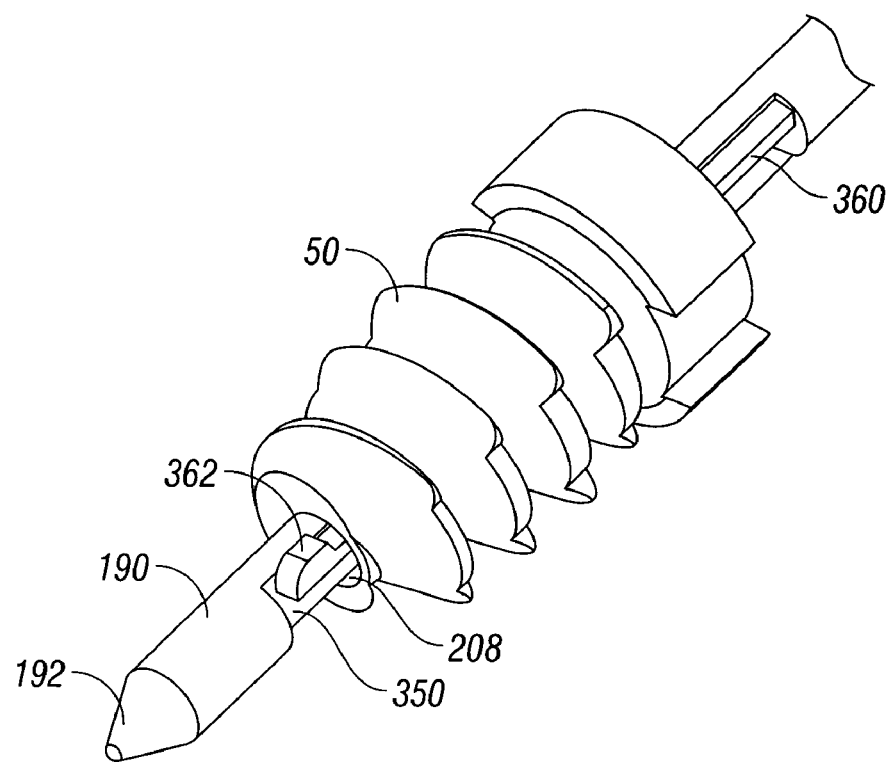
FIG. 21 is an enlarged perspective view of a distal portion of a needle of the powered tacker device in accordance with an embodiment of the present disclosure.
Figure 22:
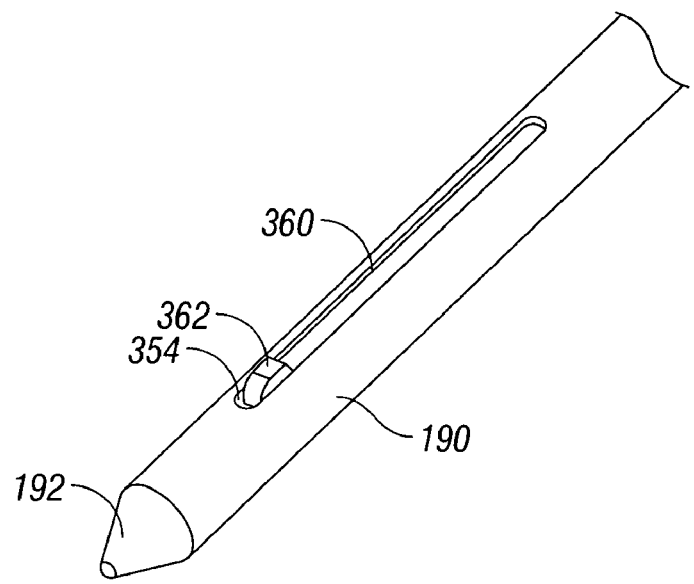
FIG. 22 in an enlarged perspective view of a distal portion of the needle of the powered tacker device in accordance with an embodiment of the present disclosure.

Other embodiments of the present disclosure are illustrated in FIGS. 21 and 22. FIG. 21 illustrates needle 190 having a cut-out portion 350 and a rod 360, and FIG. 22 illustrates needle 190 having a channel 354 and rod 360. In both embodiments, rod 360 includes a protrusion 362 adjacent its distal end and is secured to needle 190 adjacent its proximal end (e.g., via a weld). It is envisioned that rod 360 is cantilevered and its distal end is biased away from needle 190. Fastener 50 (e.g., distal-most fastener) is shown in FIG. 21 around a portion of needle 190. Protrusion 362 opposes the force exerted by spring 184 (FIG. 6), such that fastener 50 does not prematurely become ejected from powered tacker 10. To force fastener 50 past protrusion 362, rod 360 is deflected against the biasing force (e.g., downwardly in FIGS. 21 and 22) by exerting additional force on fastener 50, such that protrusion 362 is able to pass through throughbore 208 of fastener 50. After fastener 50 passes rod 360, rod 360 returns to its original biased position as the distal end of rod 360, including protrusion 362, springs away from needle 190 and is thus in a position to maintain a subsequent fastener 50 on needle 190.

Figure 23:
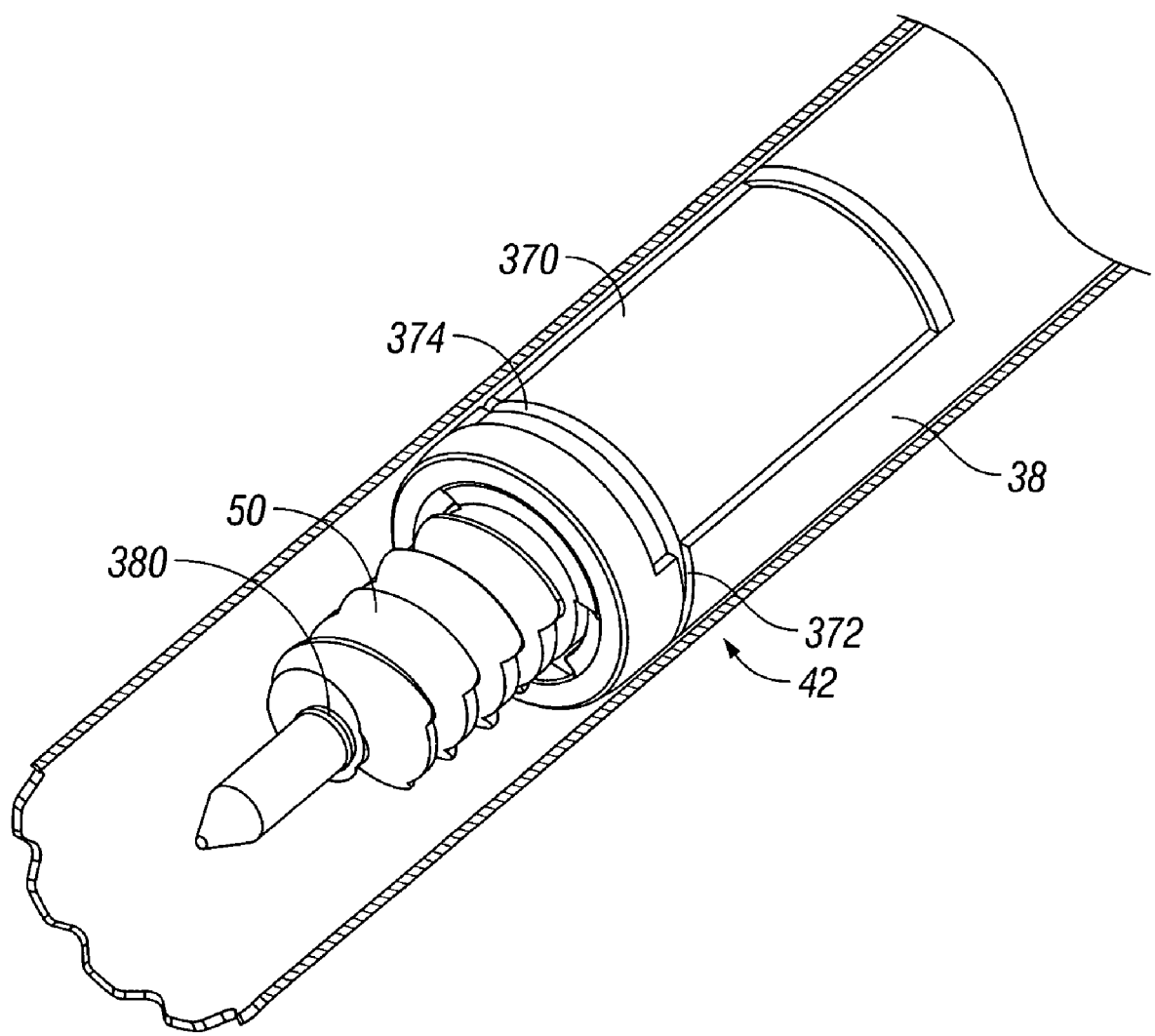
FIG. 23 is an enlarged perspective view of a distal portion of the powered tacker device in accordance with an embodiment of the present disclosure.
Figure 24:
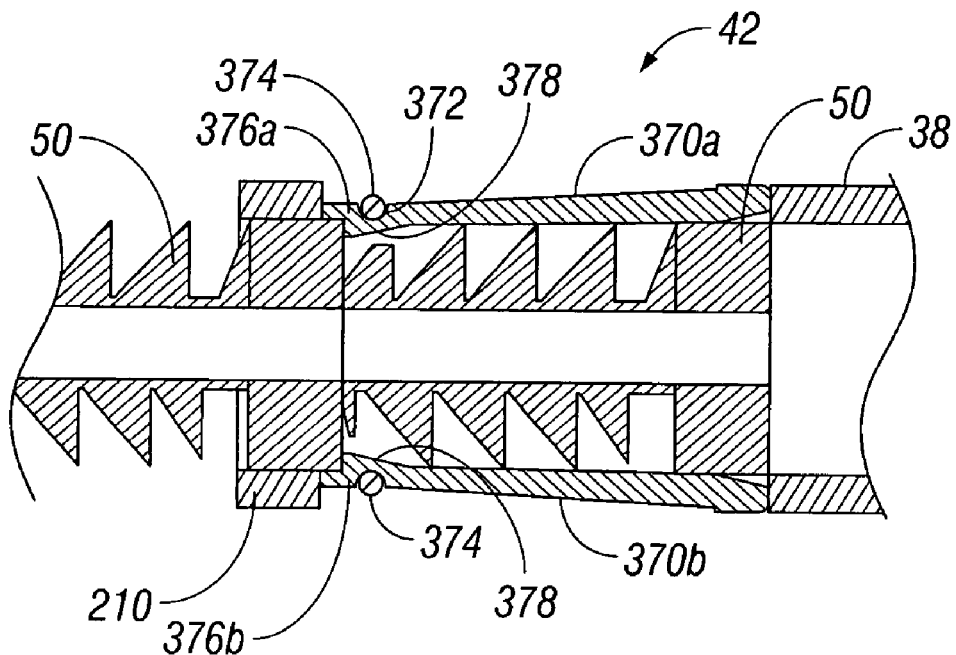
FIGS. 24 and 25 are enlarged cross-sectional views of a distal portion of the powered tacker device in accordance with an embodiment of the present disclosure.
Figure 25:
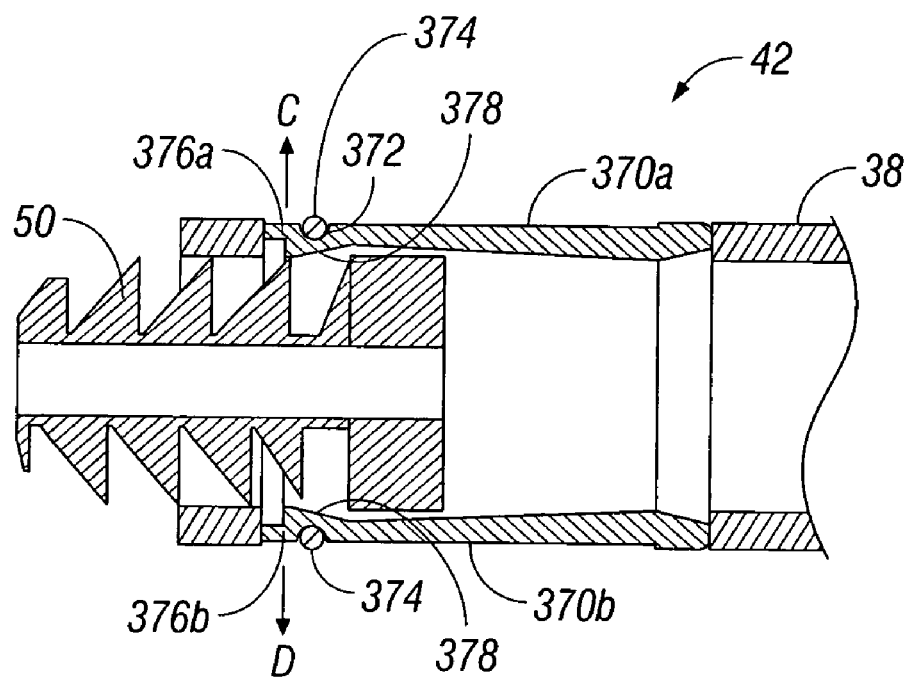

FIGS. 23-25 illustrate additional embodiments of the present disclosure. In these embodiments, a plate 370 is illustrated adjacent distal end 42 of inner tube 38. Plate 370 is shown with a plate groove 372 adjacent its distal end and plate groove 372 is configured to accept a plate ring 374 therein. Further, a needle ring 380 is shown in FIG. 23 and is disposed within a needle groove (hidden from view in FIG. 23). It is envisioned that the needle groove is dimensioned to allow needle ring 380 to be at least partially compressed therein in response to a sufficient amount of force exerted against needle ring 380. Therefore, needle ring 380 and the needle groove combine to maintain distal-most fastener 50 on needle 190 until an additional force is exerted on fastener 50 to compress needle ring 380 and push fastener 50 over and distally past needle ring 380, thus ejecting distal-most fastener 50 from needle 190.

Referring more specifically to FIGS. 24 and 25, enlarged, cross-sectional views of distal end 42 of inner tube 38 are illustrated including plate 370 thereon. Plate 370 is shown including two halves 370a and 370b, but is also envisioned that plate 370 may be a single part that is disposed around needle 190 and/or at least partially within inner tube 38. It is envisioned that a proximal portion of each plate half 370a, 370b is secured to inner tube 38, and a distal portion of each plate half 370a, 370b is floating, or otherwise unsecured, in relation to inner tube 38. Plate ring 374 encircles plates 370a, 370b within plate groove 372 and confines outward movement of plates 370a, 370b. It is also envisioned that plate ring 374 inwardly biases each plate half 370a, 370b, as illustrated in FIG. 24. Here, plate lips 376a, 376b are disposed proximal of head 210 of distal-most fastener 50, thus restricting proximal translation of distal-most fastener 50.

With reference to FIG. 25, upon distal movement of fastener 50 held adjacent plates 370a, 370b, fastener 50 forces distal portion of plates 370a, 370b outward in the direction of arrows C and D (within the confines of plate ring 374). Plates 370a, 370b are moved outward far enough to allow fastener 50 to pass therethrough and be ejected from needle 190. A ramp 378 may also be included on inner surface of each plate 370a, 370b to facilitate fastener 50 passing therethrough.

It will be understood that various modifications may be made to the embodiments disclosed herein. For example, the disclosed powered tacker devices may be provided with an AC type power source which is not self-contained within the powered tacker device. Further, the disclosed circuit board may be configured to automatically rotate the motor in the reverse direction to reset the powered tacker devices after a surgical fastener has been installed in tissue. Additionally, various other mechanisms of transferring individual fastener is from within a cartridge assembly to a driver are contemplated herein. Yet still further, the disclosed powered tacker devices may be configured so that the distal tacker assembly is removable, and or disposable, from the associated handle assembly. Therefore, the above description should not be construed as limiting, but merely as exemplifications of particular embodiments. Those skilled in the art will envision other modifications within the scope and spirit of the claims appended hereto.

The invention claimed is:

1. A powered tacker device comprising:
   a handle assembly having a power source and a drive assembly mounted within the handle assembly, the drive assembly including a keyed journal rotatably mounted within the handle assembly and rotatable in response to actuation of the power source, a drive bar longitudinally movable relative to the keyed journal and a rotator rotatable in response to rotation of the keyed journal;
   an actuator associated with the handle assembly and operable to engage the power source with the drive assembly; and
   a tacker assembly extending distally from the handle assembly and containing a plurality of surgical fasteners, the tacker assembly including an inner tube terminating in a driver engageable with the fasteners, wherein the inner tube is connected to the rotator and rotatable in response to rotation of the keyed journal,
   wherein the keyed journal includes a threaded bore and the drive bar includes a threaded outer surface engageable with the threaded bore such that rotation of the keyed journal moves the drive bar in a longitudinal direction within the handle assembly, and wherein the drive bar is connected to the rotator to move the rotator longitudinally within the handle assembly in response to rotation of the keyed journal,
   and wherein the keyed journal includes distally extending keys and the rotator includes slots engageable with the keys such that the rotator is rotated in response to rotation of the keyed journal.

2. The powered tacker device as recited in claim 1, wherein the rotator is longitudinally movable along the keys.

3. The powered tacker device as recited in claim 1, wherein the handle assembly includes a first limit switch and a second limit switch, the first and second limit switches operable to deactivate the power source.

4. The powered tacker device as recited in claim 3, wherein the drive bar includes a contact assembly, the contact assembly engageable with the first limit switch when the drive bar is in a proximal most position.

5. The powered tacker device as recited in claim 3, wherein the drive bar includes a contact assembly, the contact assembly engageable with the second limit switch when the drive bar is in a distal most position.

6. The powered tacker device as recited in claim 4, wherein the handle assembly includes at least one indicator, the indicator providing a visual indication when the contact assembly has engaged the first limit switch.

7. The powered tacker device as recited in claim 5, wherein the handle assembly includes at least one indicator, the indicator providing a visual indication when the contact assembly has engaged the second limit switch.

8. A powered tacker device comprising:
   a handle assembly having a power source and a drive assembly mounted within the handle assembly, the drive assembly including a keyed journal rotatably mounted within the handle assembly and rotatable in response to actuation of the power source, a drive bar longitudinally movable relative to the keyed journal and a rotator rotatable in response to rotation of the keyed journal;
   an actuator associated with the handle assembly and operable to engage the power source with the drive assembly; and
   a tacker assembly extending distally from the handle assembly and containing a plurality of surgical fasteners, the tacker assembly including an inner tube terminating in a driver engageable with the fasteners, wherein the inner tube is connected to the rotator and rotatable in response to rotation of the keyed journal,
   wherein the power source includes a motor engageable with the keyed journal to rotate the keyed journal and a battery to power the motor, wherein the drive assembly includes a drive gear engageable with the keyed journal, the drive gear engageable with a spur gear on the motor to rotate the keyed journal and wherein the drive assembly includes a mesh gear engageable with the keyed journal and the drive gear,
   and wherein the drive assembly includes a spring positioned within the keyed journal, the spring biasing the mesh gear into engagement with the drive gear.

9. The powered tacker device as recited in claim 1, wherein the handle assembly includes a safety mechanism, the safety mechanism preventing actuation of the power source in response to the position of an outer tube associated with the tacker assembly.

10. The powered tacker device as recited in claim 9, wherein the safety mechanism includes a safety switch actuable in response to movement of the outer tube, the safety switch preventing actuation of the power source when the outer tube is in a distal most position.

11. A powered tacker device comprising;
   a handle assembly having a power source and a drive assembly, the drive assembly mounted for rotation within the handle assembly in response to activation of the power source; and
   a tacker assembly extending distally from the handle assembly, the tacker assembly including an inner tube containing a plurality of surgical fasteners, the inner tube connected to the drive assembly and a driver mounted on the distal end of the inner tube to rotate the surgical fasteners into tissue, wherein the inner tube is rotatable a predetermined amount relative to the driver,
   wherein the tacker assembly includes a spring engageable with the inner tube and the driver to bias the inner tube relative to the driver.

12. The powered tacker device as recited in claim 11, wherein the inner tube includes longitudinally extending transfer bars configured to maintain the surgical fasteners in a predetermined orientation and the driver includes drive tabs engageable with the surgical fasteners to drive the surgical fasteners into tissue, wherein the inner tube is rotatable relative to the driver to move the transfer bars into and out of alignment with the drive tabs.

13. The powered tacker device as recited in claim 11, wherein the tacker assembly includes an outer tube frictionally engageable with the driver to prevent initial rotation of the driver during initial rotation of the inner tube.

* * * * *